United States Patent

Tanabe et al.

Patent Number: 5,861,388
Date of Patent: Jan. 19, 1999

[54] STEROID INHIBITORS OF ESTRONE SULFATASE AND ASSOCIATED PHARMACEUTICAL COMPOSITIONS AND METHODS OF USE

[75] Inventors: Masato Tanabe, Palo Alto; Richard H. Peters, San Jose; Wan-Ru Chao, Sunnyvale; Kazuhiko Shigeno, Mountain View, all of Calif.

[73] Assignee: SRI International, Menlo Park, Calif.

[21] Appl. No.: 1,601

[22] Filed: Dec. 31, 1997

Related U.S. Application Data

[62] Division of Ser. No. 794,229, Jan. 29, 1997, Pat. No. 5,763,432.

[51] Int. Cl.$^6$ .............................. A61K 31/58; C07J 71/00
[52] U.S. Cl. .............................................. 514/176; 540/55
[58] Field of Search ................................. 540/55; 514/176

[56] References Cited

U.S. PATENT DOCUMENTS

| | | | |
|---|---|---|---|
| 3,033,860 | 5/1962 | Kuehne | 260/239.55 |
| 4,297,350 | 10/1981 | Babcock et al. | 424/238 |

FOREIGN PATENT DOCUMENTS

WO93/05064  3/1993  WIPO .

OTHER PUBLICATIONS

Howarth et al., (1994) "Estrone Sulfamates: Potent Inhibitors of Estrone Sulfatase with Therapeutic Potential," *J. Med. Chem.* 37:219–221.

*Primary Examiner*—José G. Dees
*Assistant Examiner*—Barbara Bodio
*Attorney, Agent, or Firm*—Dianne E. Reed; Bozicevic & Reed LLP

[57] ABSTRACT

Novel compounds useful as inhibitors of estrone sulfatase are provided. The compounds have the structural formula (I)

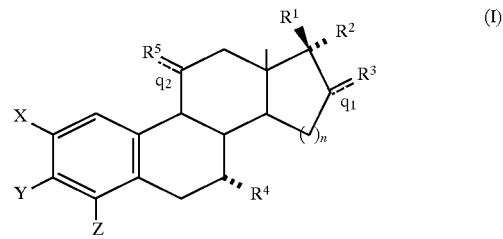

wherein X and Y, or Y and Z, form an oxathiazine dioxide ring or a dihydro-oxathiazine dioxide ring, and the other various substituents are as defined herein. Pharmaceutical compositions and methods for using the compounds of formula (I) to treat estrogen-dependent disorders are provided as well.

22 Claims, No Drawings

STEROID INHIBITORS OF ESTRONE SULFATASE AND ASSOCIATED PHARMACEUTICAL COMPOSITIONS AND METHODS OF USE

CROSS-REFERENCE TO RELATED APPLICATIONS

This is a divisional of U.S. patent application Ser. No. 08/794,229, filed Jan. 29, 1997, now U.S. Pat. No. 5,763,432.

TECHNICAL FIELD

The present invention relates generally to steroid hormones, and more specifically relates to novel steroids which are inhibitors of the enzyme estrone sulfatase. The

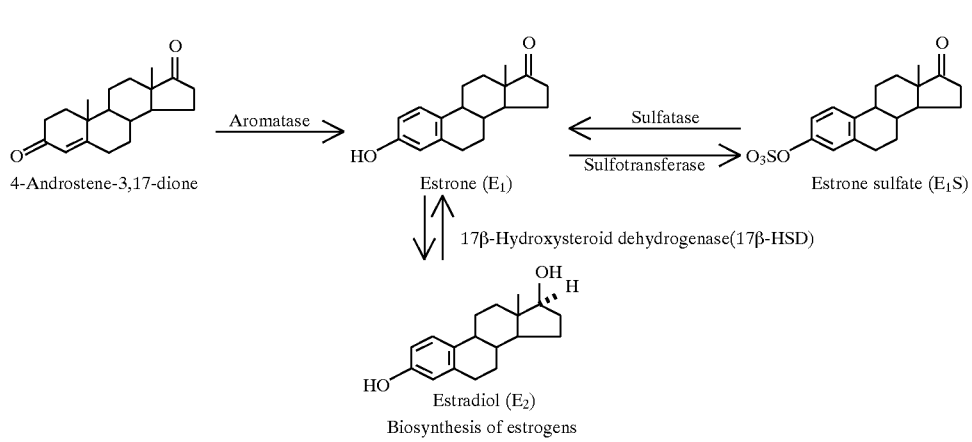

Biosynthesis of estrogens invention additionally relates to methods for inhibiting estrone sulfatase activity, to treatment of disorders that are estrogen-dependent, i.e., are estrogen-induced or estrogen-stimulated, and to pharmaceutical compositions containing one or more of the novel compounds.

BACKGROUND

Breast cancer is one of the most prevalent types of cancer, and epidemiological and clinical studies have shown that approximately one-third of breast tumors are estrogen-dependent. This means that estrogens are required for the growth of such breast tumors in both premenopausal and postmenopausal patients. In postmenopausal women, in whom breast cancer most commonly occurs, breast tumor concentrations of estrone and estradiol are considerably higher than blood estrogen levels. Although retention of estrogens in breast tumors by high-affinity binding proteins contributes to the level of estrogens in tumors, estrogen concentrations in the breast are higher than plasma levels in breast cancer patients regardless of whether their tumors are estrogen receptor-positive (ER+) or receptor-negative (ER-). In situ formation of estrogen from estrogen biosynthetic precursors within tumors is now known to make a major contribution to the estrogen content of breast tumors.

The enzymes required for estradiol biosynthesis (i.e., aromatase, 17β-hydroxy-steroid dehydrogenase, and estrone sulfatase) are present in normal and malignant breast tissues. Blood concentrations of estrone sulfate are 8- to 10-fold greater than those of unconjugated free estrone, and breast tissue concentrations of estrone sulfatase activity, the enzyme responsible for the conversion of estrone sulfate to estrone, are a thousand-fold higher than those of aromatase activity. Together, these findings suggest that estrone sulfatase plays a key role in regulating the formation of estrogens within breast tumors, particularly in postmenopausal women. See, e.g.: Pasqualini et al., *Ann. N.Y. Acad. Sci.* 464:106–116 (1986); Santner et al., *J. Clin. Endocrinol. Metabol.* 59(1):29–33 (1984); Evans et al., *J. Steroid Biochem. Mol. Biol.* 39:493–499 (1991); Pasqualini et al., *J. Steroid Biochem. Mol. Biol.* 41(308):323–329 (1992); Vignon et al., *Endocrinology* 106(4):1079–1086 (1980); and Santner et al., *Int. J. Cancer* 54:119–124 (1993).

There is additional evidence of the relative significance of the aromatase pathway and the estrone sulfatase pathway in providing sufficient estrogen to sustain tumor growth. In postmenopausal women, the levels of estradiol in breast tumor tissues are 10 to 40 times higher than in plasma and are similar to those in premenopausal women, even though plasma estrogen levels are much lower after the menopause. This concentration gradient is not entirely due to estradiol uptake and binding to estrogen receptors, since tissue estradiol levels correlate poorly with estrogen receptor levels.

In situ production of estradiol, through either the aromatase or the estrone sulfatase pathway, could affect this gradient. The level of estrone sulfate present in the serum of postmenopausal women is 10 times higher than the level of free estrogens (Prost et al., *Cancer Res.* 44:661–664 (1984)). Serum estrone sulfate levels are also higher in postmenopausal women with breast cancer than in normal postmenopausal women (Purohit et al., *Int. J. Cancer* 50:901–905 (1992)). Also, sulfatase levels in tumors are much higher than aromatase levels (Pasqualini et al., *J. Steroid Biochem.* 34(1–6):155–163 (1989); Adams et al., *Cancer Res.* 39:5124–5126 (1979)). The absolute levels of aromatase activity in tumors are relatively low, ranging from 5 to 80 pmol/g protein/h. Bradlow (Bradlow et al., *Cancer Res. (Suppl.)* 42:3382s–3386s (1982)) and others consider this degree of tumor aromatase activity too low for a biologically meaningful level of estradiol to be synthesized locally within the tumor.

Quantitative information on the local production of estrogen shows that the sulfatase activity in breast tumors is more than 10 times the aromatase activity. When sulfatase and aromatase activity in human tumors were compared at physiological levels of substrate, sulfatase produced 2.8 pmol estrone/g protein/h while aromatase produced only 0.27 pmol/g protein/h. Consequently, estrone sulfate represents one of the most important precursors for tissue production of estradiol, and estrone sulfatase is a quantitatively more important local route for estrogen production than aromatase.

To date, little work has been done in the development of estrone sulfatase inhibitors. Li et al., *Steroids* 60 (March 1995), at pages 299–306, evaluate several compounds as potential inhibitors of human placental sterylsulfatase, but do not identify any highly potent estrone sulfatase inhibitors. Similarly, Duncan et al., *Cancer Research* 53:298–303 (1993), evaluate a potential estrone sulfatase inhibitor, estrone-3-methylthiophosphonate, but conclude that the experimental work done with that compound would hopefully lead to development of "more efficient" inhibitors of the enzyme.

Accordingly, the present invention is directed to novel compounds that are extremely effective estrone sulfatase inhibitors. The invention thus represents a significant advance in the art, particularly in the treatment of breast cancer and other diseases and conditions that are potentiated by the presence of estrogens.

In addition to the aforementioned references, the following pertain to one or more aspects of the invention and as much may be of background interest to those skilled in the art: Howarth et al., *J. Med. Chem.* 37:219–221 (1994) and PCT Publication No. WO93/05064 relate to estrone sulfamates as inhibitors of steroid sulfatases, with Howarth et al. specifically focused on inhibition of estrone sulfatase; and U.S. Pat. Nos. 3,033,860 to Kuehne and 4,297,350 to Babcock et al., which describe steroids having an additional cyclic structure adjacent to the "A" ring.

No art of which applicants are aware, however, describe compounds as provided herein, to inhibit estrone sulfatase or for any other purpose. To the best of applicants' knowledge, then, the compounds and methods of the invention are previously unknown and completely unsuggested by the art.

SUMMARY OF THE INVENTION

Accordingly, it is a primary object of the invention to address the above-mentioned need in the art by providing novel compounds useful as inhibitors of estrone sulfatase.

It is another object of the invention to provide a method for inhibiting estrone sulfatase activity using the novel compounds.

It is still another object of the invention to provide a method for treating an individual with a disorder that is estrogen-dependent, i.e., an estrogen-induced or estrogen-stimulated condition or disease, by administering to the individual an effective estrone sulfatase inhibiting amount of a novel compound as provided herein, or a pharmaceutically acceptable salt thereof.

It is a further object of the invention to provide a pharmaceutical composition for treating an individual with a disorder that is estrogen-dependent, the composition comprising a pharmaceutically acceptable carrier and an effective estrone sulfatase inhibiting amount of a novel compound as provided herein or a pharmaceutically acceptable salt thereof.

Additional objects, advantages and novel features of the invention will be set forth in part in the description which follows, and in part will become apparent to those skilled in the art upon examination of the following, or may be learned by practice of the invention.

In one embodiment, the invention relates to novel compounds having the structure of Formula (I)

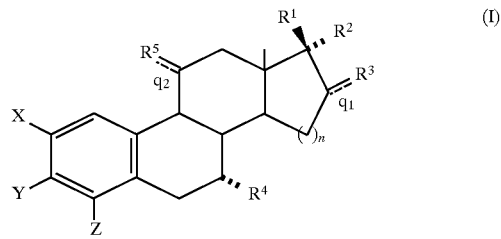

wherein:

n is 1 or 2;

$R^1$ and $R^2$ are different, and are selected from the group consisting of hydrogen, lower alkyl, lower alkynyl, and $OR^6$ where $R^6$ is hydrogen, lower alkyl or —(CO)—$R^7$ where $R^7$ is lower alkyl, or wherein $R^1$ and $R^2$ together form =O, =S, or =C($R^8R^9$) in which $R^8$ and $R^9$ are independently selected from the group consisting of hydrogen, —CHO, lower alkyl, and cyano, or together form a =$CH_2$ substituent;

$R^3$ is hydrogen, halogen or lower alkyl, or, when the dotted line at $q_1$ indicates the presence of a double bond, is $CH_2$;

$R^4$ is selected from the group consisting of hydrogen and lower alkyl;

$R^5$ is selected from the group consisting of hydrogen, hydroxyl, lower alkyl, lower alkenyl, lower alkoxy, and aryl, or when the dotted line at $q_2$ indicates the presence of a double bond, is $CH_2$; and either X and Y are linked to form an oxathiazine dioxide ring or a dihydro-oxathiazine dioxide ring, if dihydro-oxathiazine, having a substituent $R^{10}$ on the carbon atom ortho to the A ring, wherein $R^{10}$ is hydrogen, lower alkyl, lower alkynyl or monocyclic aryl, but is preferably hydrogen, and Z is hydrogen, or Y and Z are linked to form an oxathiazine dioxide ring or a dihydro-oxathiazine dioxide ring, if dihydro-oxathiazine, containing a substituent $R^{10}$ as defined above, and X is hydrogen, cyano, lower alkyl, lower alkenyl, lower alkynyl, lower alkoxy, nitro, —$COOR^{11}$, or —($CH_2$) $NR^{12}R^{13}$ wherein $R^{11}$, $R^{12}$ and $R^{13}$ are independently hydrogen or lower alkyl, and pharmaceutically acceptable salts and esters thereof.

The invention also relates to pharmaceutical compositions containing one or more compounds of structural formula (I), and further relates to methods of using the compounds to inhibit estrone sulfatase activity and to treat individuals with disorders that are estrogen-dependent.

DETAILED DESCRIPTION OF THE INVENTION

Definitions and Nomenclature:

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an estrone sulfatase inhibitor" includes mixtures of estrone sulfatase inhibitors, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Preferred alkyl groups herein contain 1 to 12 carbon atoms. The term "lower alkyl" intends an alkyl group of one to six carbon atoms, preferably one to four carbon atoms.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 1 to 12 carbon atoms. The term "lower alkenyl" intends an alkenyl group of one to six carbon atoms, preferably one to four carbon atoms. The term "cycloalkenyl" intends a cyclic alkenyl group of three to eight, preferably five or six, carbon atoms.

The term "alkynyl", as used herein refers to a branched or unbranched hydrocarbon group of 2 to 24 carbon atoms containing at least one triple bond, such as ethynyl, n-propynyl, isopropynyl, n-butynyl, isobutynyl, t-butynyl, octynyl, decynyl and the like. Preferred alkynyl groups herein contain 1 to 12 carbon atoms. The term "lower alkynyl" intends an alkynyl group of one to six carbon atoms, preferably one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "acyl" is used in its conventional sense to refer to a molecular substituent RCO— where R is alkyl as defined above. The term "lower acyl" refers to an acyl group wherein R contains one to six, more preferably one to four, carbon atoms.

The term "aryl" as used herein refers to a monocyclic aromatic species of 5 to 7 carbon atoms, and is typically phenyl. Optionally, these groups are substituted with one to four, more preferably one to two, lower alkyl, lower alkoxy or hydroxyl substituents.

The term "inhibitor" as used herein is intended to include both reversible enzyme inhibitors and irreversible enzyme inhibitors, i.e., enzyme inactivators.

"Optional" or "optionally" means that the subsequently described event or circumstance may or may not occur, and that the description includes instances where said event or circumstance occurs and instances where it does not. For example, the phrase "optional presence of a double bond" to refer to the dotted line in the structure of formula (I) means that either a single bond or a double bond is present. Similarly, the phrase "optionally substituted" as in "optionally substituted dihydro-oxathiazine dioxide ring" means that a non-hydrogen substituent may or may not be present, and the description includes structures wherein a non-hydrogen substituent is present and structures wherein a non-hydrogen substituent is not present.

By the terms "effective amount" or "pharmaceutically effective amount" or "estrone sulfatase inhibiting amount" of an agent as provided herein are meant a nontoxic but sufficient amount of the agent to provide the desired level of enzyme inhibition and corresponding therapeutic effect. As will be pointed out below, the exact amount required will vary from subject to subject, depending on the species, age, and general condition of the subject, the severity of the condition being treated, and the particular enzyme inhibitor and mode of administration, and the like. Thus, it is not possible to specify an exact "effective amount". However, an appropriate "effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected estrone sulfatase inhibitor without causing any undesirable biological effects or interacting in a deleterious manner with any of the other components of the pharmaceutical composition in which it is contained. Similarly, a "pharmaceutically acceptable" salt or a "pharmaceutically acceptable" ester of a novel compound as provided herein is a salt or ester which is not biologically or otherwise undesirable.

In describing the location of groups and substituents, the following numbering systems will be employed. This system is intended to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

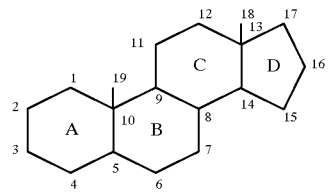

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α" denoted by a broken line, indicates that the group in question is below the general plane of the molecule as drawn, and "β," denoted by a bold line, indicates that the group at the position in question is above the general plane of the molecule as drawn.

In addition, the five- and six-membered rings of the steroid molecule are often designated A, B, C and D as shown.

The Novel Compounds:

The novel compounds provided herein are those defined by structural formula (I), wherein n, $R^1$, $R^2$, $R^3$, $R^4$, $R^5$, X, Y and Z are as defined above.

Preferred compounds within this group are wherein one of $R^1$ and $R^2$ is hydrogen, and the other is selected from the group consisting of hydroxyl, lower alkyl, lower alkoxy, lower acyl and ethynyl, or wherein $R^1$ and $R^2$ together form =O or =C($R^8R^9$) in which $R^8$ and $R^9$ are independently selected from the group consisting of hydrogen, —CHO, methyl, ethyl, n-propyl, and cyano, or together form a =$CH_2$ substituent.

Also, as explained above, X and Y may be linked to form an oxathiazine dioxide ring or a dihydro-oxathiazine dioxide ring, if dihydro-oxathiazine, bearing a substituent $R^{10}$ on the carbon atom of the ring adjacent to the A ring, wherein $R^{10}$ is hydrogen, lower alkyl, lower alkynyl or monocyclic aryl. Examples of specific $R^{10}$ substituents, then, in addition to hydrogen, include methyl, ethynyl and phenyl. In this embodiment, when X and Y are linked, Z is hydrogen. These compounds, wherein X and Y are linked to form an oxathiazine dioxide ring or a dihydro-oxathiazine dioxide ring which may or may not be substituted have the structural formulae (II) and (III) respectively:

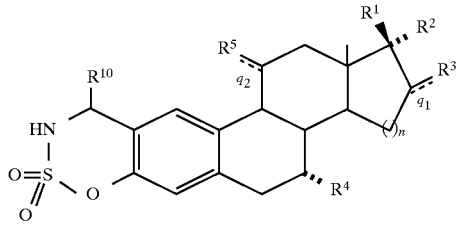
(II)

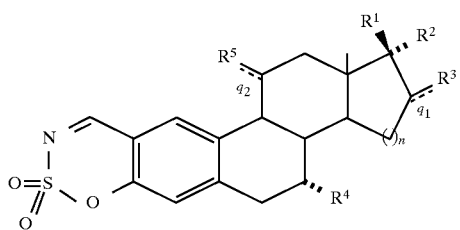
(III)

Alternatively, Y and Z may be linked to form an oxathiazine dioxide ring or a dihydro-oxathiazine dioxide ring, and, as above, if the ring is "dihydro," again, it contains a substituent $R^{10}$ present on the carbon atom adjacent to the A ring, wherein $R^{10}$ is hydrogen, lower alkyl, lower alkynyl or monocyclic aryl. Examples of specific $R^{10}$ groups are as set out above with respect to a heterocyclic ring formed from X and Y. In this case, when Y and Z are linked, X may be hydrogen, cyano, lower alkyl, lower alkenyl, lower alkynyl, lower alkoxy, nitro, —$COOR^{11}$, or —$(CH_2)NR^{12}R^{13}$ wherein $R^{11}$, $R^{12}$ and $R^{13}$ are independently hydrogen or lower alkyl.

These latter compounds, wherein Y and Z are linked to form an oxathiazine dioxide ring or a dihydro-oxathiazine dioxide ring which may or may not be substituted have the structural formulae (IV) and (V) respectively:

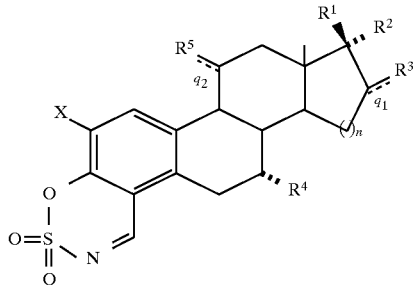
(IV)

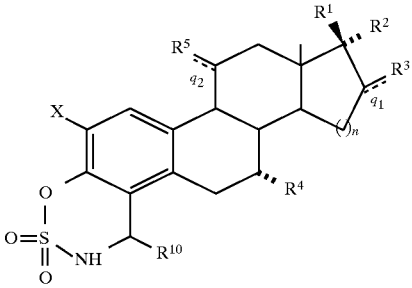
(V)

Examples of specific compounds of formula include, but are not limited to, the following:

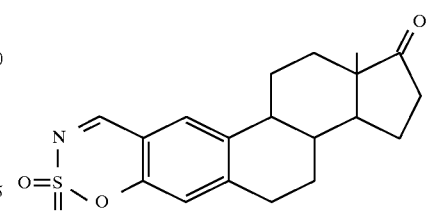

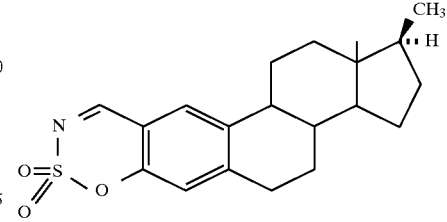

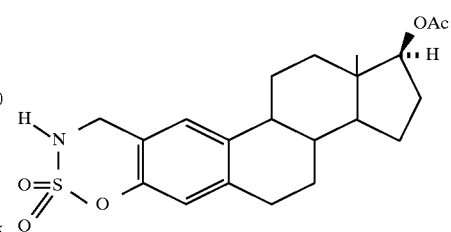

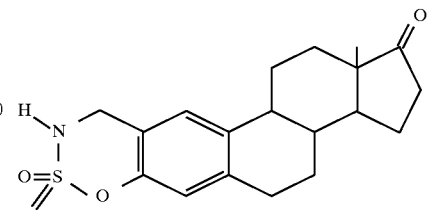

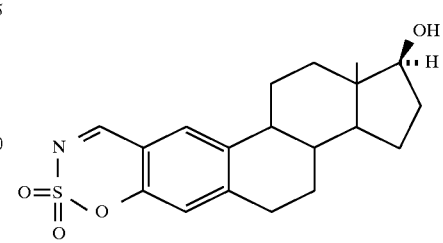

9
-continued

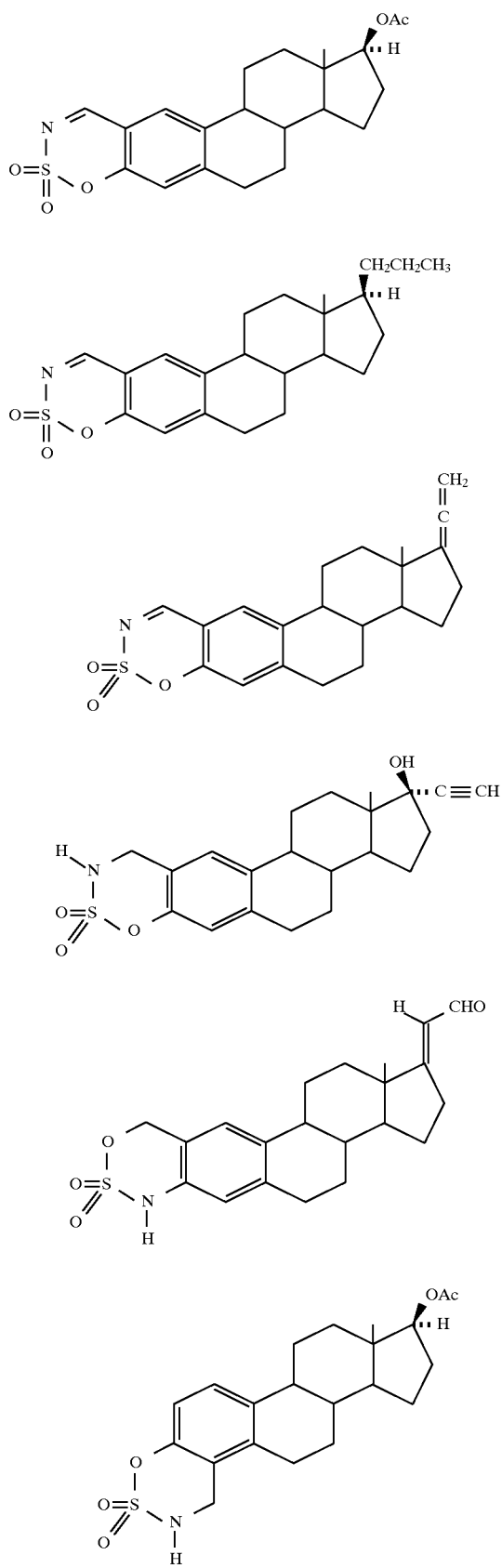

10
-continued

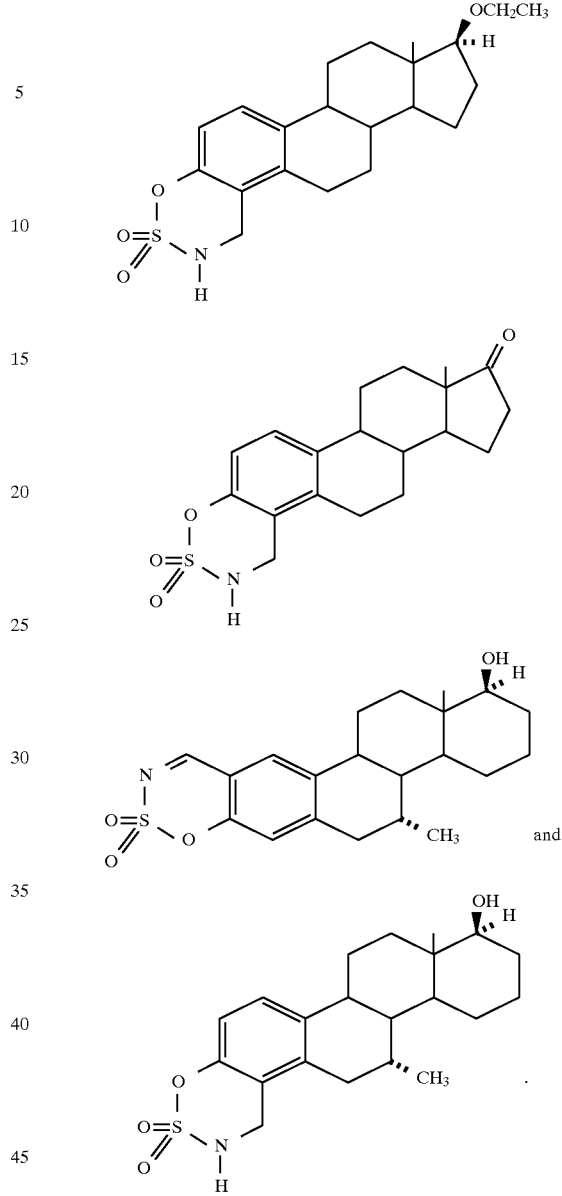

The novel compounds also include pharmaceutically acceptable salts and esters of compounds of Formula (I), as explained in the next section.

Utility and Administration:

The compounds defined by structural formula (I) are useful as estrone sulfatase inhibitors and are therefore useful for the treatment of estrogen-dependent disorders, i.e., conditions or diseases that are estrogen-induced or estrogen stimulated. Since the present compounds can lower circulating estrogen levels, they can effectively prevent the biologically active estrogens from reaching endocrine tumors. In addition, since the present compounds can reduce estrogen biosynthesis in tumors capable of endogenous estrogen synthesis, the present compounds are capable of inducing remissions in breast cancer, including metastatic tumors. Furthermore, the present compounds have utility in the treatment of ovarian, uterine and pancreatic tumors as well as disease conditions such as galactorrhea, McCurne-Albright syndrome, benign breast disease, and endometriosis.

The compounds may be conveniently formulated into pharmaceutical compositions composed of one or more of the compounds in association with a pharmaceutically acceptable carrier. See *Remington's Pharmaceutical Sciences* (Mack Publ. Co., Easton, Pa.), which discloses typical carriers and conventional methods of preparing pharmaceutical compositions which may be used to prepare formulations using the novel enzyme inhibitors of the invention. The compounds may also be administered in the form of pharmaceutically acceptable salts, or in the form of pharmaceutically acceptable esters. Salts of the compounds may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Preparation of esters involves functionalization of hydroxyl and/or carboxyl groups which may be present at various positions on the steroid molecule. These esters may derive from organic acid or inorganic acid functionalities at those positions, but are typically acyl-substituted derivatives of free alcohol groups, i.e., moieties which are derived from carboxylic acids of the formula RCOOH where R is alkyl, and preferably is lower alkyl.

The compounds may be administered orally, parenterally (e.g., intravenously), topically, transdermally, by intramuscular injection, or by intraperitoneal injection, or the like, although oral administration is preferred for those compounds which have oral activity. The amount of active compound administered will, of course, be dependent on the subject being treated, the subject's weight, the manner of administration and the judgment of the prescribing physician. Generally, however, dosage will be in the range of approximately 0.01 mg/kg/day to 10.0 mg/kg/day, more preferably in the range of about 1.0 mg/kg/day to 5.0 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectable formulations can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795.

Process for Preparation:

The compounds of the invention may be prepared in high yield using relatively simple, straightforward methods as exemplified in the experimental section herein. Synthesis of representative compounds are detailed in Examples.

Experimental

The practice of the present invention will employ, unless otherwise indicated, conventional techniques of synthetic organic chemistry, biological testing, and the like, which are within the skill of the art. Such techniques are explained fully in the literature. See, e.g., Fieser et al., *Steroids* (New York: Reinhold, 1959), Djerassi, *Steroid Reactions: An Outline for Organic Chemists* (San Francisco: Holden-Day, 1963), and Fried et al., *Organic Reactions in Steroid Chemistry*, vols. 1 and 2 (New York: Reinhold, 1972), for detailed information concerning steroid-related synthetic procedures. Reference may be had to MacIndoe et al., *Endocrinology* 123(3):1281–1287 (1988), Duncan et al., *Cancer Res.* 53:298–303 (1993), and Yue et al., *J. Steroid Biochem.* 44:671–673 (1993), for a description of the biological testing procedures useful to evaluate compounds such as those described and claimed herein. All patents, patent applications, and publications mentioned herein, both supra and infra, are hereby incorporated by reference.

It is to be understood that while the invention has been described in conjunction with the preferred specific embodiments thereof, that the description above s well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C and pressure is at or near atmospheric. All solvents were purchased as HPLC grade, and all reactions were routinely conducted under an inert atmosphere of argon unless otherwise indicated. All reagents were obtained commercially unless otherwise indicated. Estrone and estradiol were purchased from Berlichem U.S.; ethynyl estradiol was purchased from Akzo Nobel. NMR analyses were conducted on either a Varian Gemini 300 and were referenced to chloroform at $\delta$ 7.27. FTIR spectra were recorded on a Perkin-Elmer 1610.

Preparation of 17β-Acetoxyestra-1,3,5(10)-trieno-[3,2,e]-1',2',3'-oxathiazine-2',2'-dioxide (4)

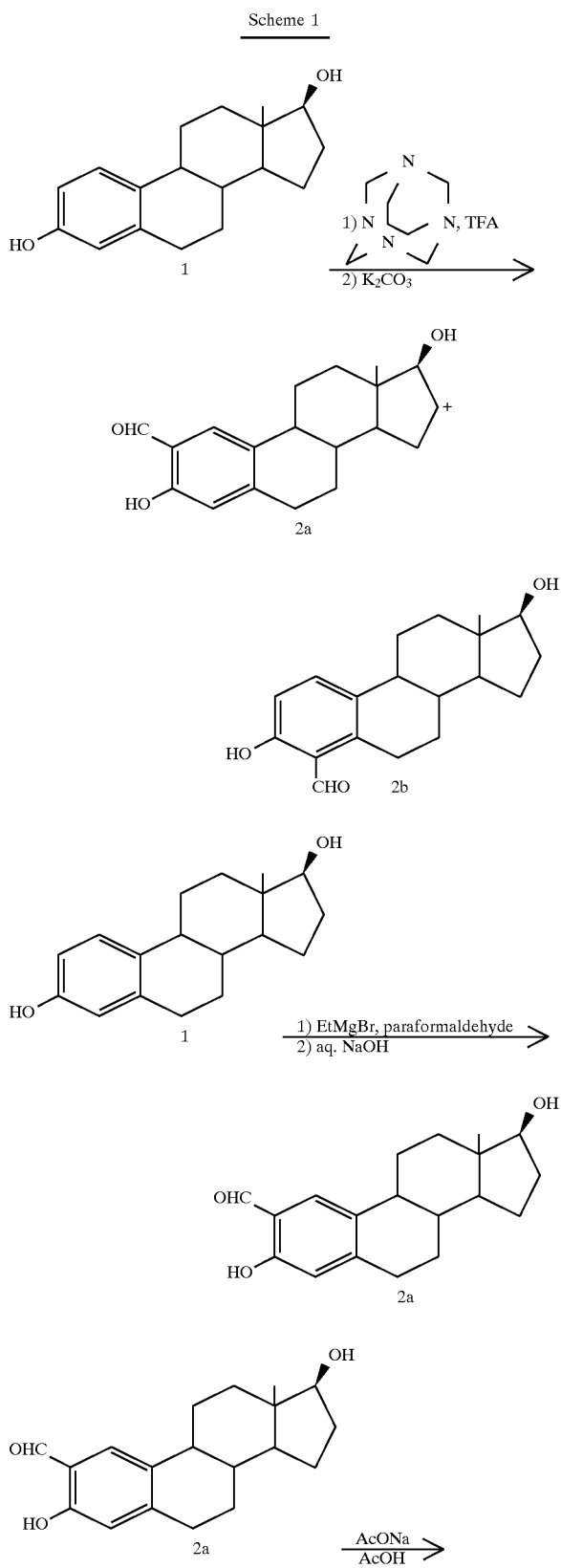

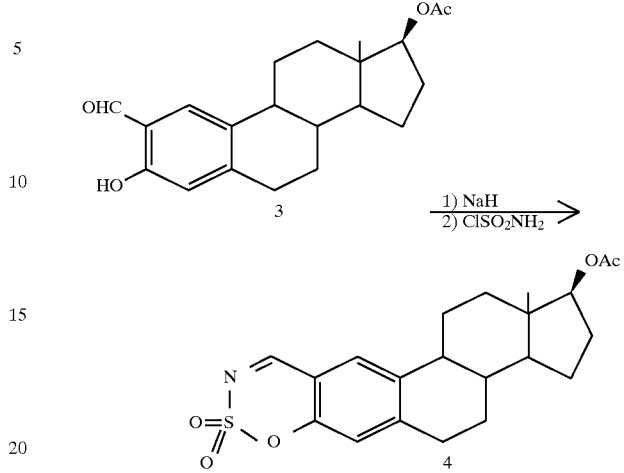

(a) Synthesis of 3,17β-dihydroxyestra-1,3,5(10)-triene-2-carboxaldehyde (2a) and 3,17β-dihydroxyestra-1,3,5(10)-triene-4-carboxaldehyde (2b):

To a mixture of estradiol (1, 13.6 g, 50 mmol) and hexamethylenetetramine (21.0 g, 150 mmol) was added trifluoroacetic acid (100 mL) at room temperature. The reaction mixture was stirred for 6 h at 100° C., poured into $H_2O$ (300 mL), and extracted with $Et_2O$. The combined organic layers were washed with $H_2O$, then with saturated aqueous NaCl, and dried ($MgSO_4$). The desiccant was filtered and the solvent was evaporated at reduced pressure. The residue was dissolved in THF (50 mL) and MeOH (50 mL), potassium carbonate (6.9 g, 50 mmol) was added, and the mixture stirred for 1 h at room temperature. The reaction mixture was then diluted with EtOAc, acidified with 1N HCl, and extracted with EtOAc. The combined organic layers were washed with $H_2O$, then with saturated aqueous NaCl, and dried ($MgSO_4$). The desiccant was filtered and the solvent was evaporated at reduced pressure. The residue was purified by column chromatography (silica gel) using n-hexane:THF (5:1→3:1, v/v) to afford 1.91 g of 2a (13% yield), m.p. 219°–221° C., and 0.552 g of 2b (4% yield), m.p. 146°–147° C.

2a: $^1H$ NMR: δ 10.77 (s, 1H, —OH), 9.81 (s, 1H, —CHO), 7.42 (s, 1H, aromatic), 6.70 (s, 1H, aromatic), 3.74 (t, 1H, 17α-H), 0.79 (s, 3H, 18-$CH_3$); MS (EI): m/z 300 ($M^+$).

2b: $^1H$ NMR: δ 12.03 (s, 1H, —OH), 10.42 (s, 1H, —CHO), 7.53 (d, 1H, aromatic), 6.83 (d, 1H, aromatic), 3.79 (t, 1H, 17α-H), 0.84 (s, 3H, 18-$CH_3$); MS (EI): m/z 300 ($M^+$).

(b) Alternative preparation of 2a: To a suspension of magnesium (2.07 g, 85 mmol) in THF (20 mL) was added bromoethane (8.9 mL, 119 mmol) dissolved in THF (15 mL) at room temperature. Estradiol (1, 4.63 g, 17 mmol) dissolved in THF (40 mL) was added to the reaction mixture, and stirring continued for 30 min. The solvent was removed at reduced pressure, and to the residue were added benzene (200 mL), hexamethylphosphoric triamide (7.4 mL, 42.5 mmol) and paraformaldehyde (7.00 g). Stirring was continued for 20 h at 80° C. After the reaction mixture was cooled to room temperature, 5N HCl (150 mL) was added and the mixture extracted with EtOAc. The combined organic layers were washed with $H_2O$, then with saturated aqueous NaCl, and dried (Na$_2$SO$_4$). The desiccant was filtered and the solvent was evaporated at reduced pressure. The residue was dissolved in MeOH (200 mL), 20% aqueous sodium hydroxide (25 mL) added, and the mixture stirred for 30 min at room temperature. The reaction mixture was acidified with 5N HCl at 0° C., the solvent evaporated at reduced pressure, and the residue extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:THF (5:1→2:1, v/v) to afford 4.81 g of 2a (94% yield).

$^1$H NMR: δ 10.77 (s, 1H, —OH), 9.81 (s, 1H, —CHO), 7.42 (s, 1H, aromatic), 6.70 (s, 1H, aromatic), 3.74 (t, 1H, 17α-H), 0.79 (s, 3H, 18-CH$_3$); MS (EI): m/z 300 (M$^+$).

(c) Synthesis of 3,17β-dihydroxyestra-1,3,5(10)-triene-2-carboxaldehyde 17-acetate (3):

To a suspension of 3,17β-dihydroxyestra-1,3,5(10)-triene-2-carboxaldehyde (2a, 0.150 g, 0.50 mmol) in acetic acid (3.0 mL) was added sodium acetate (0.600 g, 7.5 mmol) at room temperature. The reaction mixture was stirred for 24 h under reflux. After the reaction mixture was cooled to room temperature, it was deluted with EtOAc, washed with H$_2$O, then with saturated aqueous NaCl, and dried (MgSO$_4$). The desiccant was filtered and the solvent was evaporated at reduced pressure. The residue was purified by column chromatography (silica gel) using n-hexane:EtOAc (5:1, v/v) to afford 0.144 g of 3 (84% yield), m.p. 184°–185° C.

$^1$H NMR: δ 10.82 (s, 1H, —OH), 9.86 (s, 1H, —CHO), 7.47 (s, 1H, aromatic), 6.75 (s, 1H, aromatic), 4.75 (t, 1H, 17α-H), 2.11 (s, 3H, —OCOCH$_3$), 0.89 (s, 3H, 18-CH$_3$); MS (EI): m/z 342 (M$^+$).

(d) Synthesis of 17β-acetoxyestra-1,3,5(10)-trieno-[3,2,e]-1',2',3'-oxathiazine-2',2'-dioxide (4):

To a solution of chlorosulfonyl isocyanate (0.17 mL, 1.9 mmol) in CH$_2$Cl$_2$ (1.5 mL) was added formic acid (0.38 mL of a CH$_2$Cl$_2$ solution, 5.0M, 1.9 mmol) at 0° C. The reaction mixture was warmed to room temperature and stirred for 1 h. To a solution of 3,17β-dihydroxyestra-1,3,5(10)-triene-2-carboxaldehyde 17-acetate (3, 0.133 g, 0.39 mmol) in DMF (5.0 mL) was added sodium hydride (0.031 g of a mineral oil dispersion, 60%, 0.78 mmol) at 0° C. The reaction mixture was stirred for 1 h, the pre-prepared reagent was added, and stirring continued for 5 h at room temperature. The reaction mixture was quenched with saturated aqueous NH$_4$Cl at 0° C., then extracted with EtOAc. The combined organic layers were washed with H$_2$O, then with saturated aqueous NaCl, and dried (MgSO$_4$). The desiccant was filtered and the solvent was evaporated at reduced pressure. The residue was purified by column chromatography (silica gel) using n-hexane:acetone (4:1→3:1, v/v) to afford 0.084 g of the starting material 3 (63% yield) and 0.029 g of 4 (19% yield), m.p. 202°–203° C.

$^1$H NMR: δ 8.62 (s, 1H, —CH=N—), 7.57 (s, 1H, aromatic), 7.03 (s, 1H, aromatic), 4.75 (t, 1H, 17α-H), 2.10 (s, 3H, —OCOCH$_3$), 0.88 (s, 3H, 18-CH$_3$); MS (EI): m/z 403 (M$^+$). HRMS calcd. for C$_{21}$H$_{26}$N$_1$O$_5$S$_1$, 404.1532; found, 404.1525.

EXAMPLE 2

Preparation of Estra-1,3,5(10)-trien-17-ono-[3,2,e]-1',2',3'-oxathiazine-2',2'-dioxide (6)

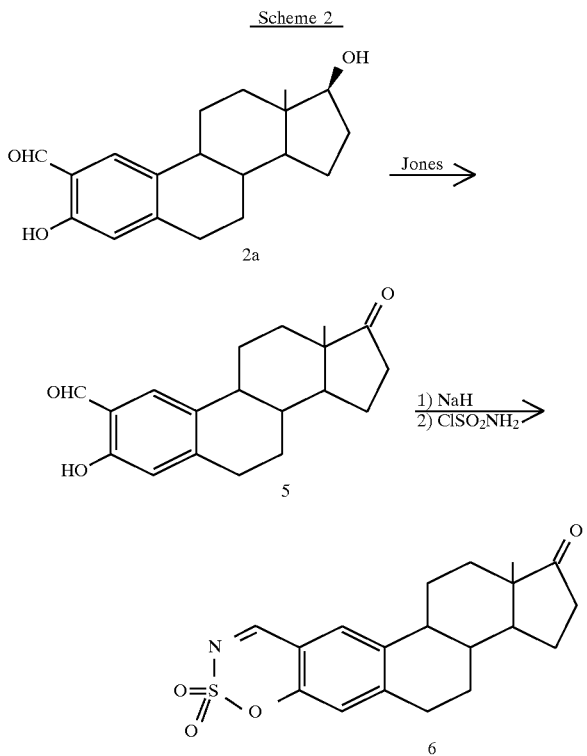

Scheme 2

(a): Synthesis of 3-hydroxyestra-1,3,5(10)-trien-17-one-2-carboxaldehyde (5):

To a solution of 3,17β-dihydroxyestra-1,3,5(10)-triene-2-carboxaldehyde (2a, 0.300 g, 1.0 mmol) in acetone (20 mL) was added Jones reagent (0.5 mL) at 0° C. The reaction mixture was stirred for 5 min, then quenched with 2-propanol, and extracted with EtOAc. The combined organic layers were washed with H$_2$O, then with saturated aqueous NaCl, and dried (MgSO$_4$). The desiccant was filtered and the solvent was evaporated at reduced pressure. The residue was purified by column chromatography (silica gel) using n-hexane:THF (4:1→3:1, v/v) to approximately 0.185 g of 5 (62% yield), m.p. 154°–157° C.

$^1$H NMR: δ 10.83 (s, 1H, —OH), 9.86 (s, 1H, —CHO), 7.47 (s, 1H, aromatic), 6.77 (s, 1H, aromatic), 0.97 (s, 3H, 18-CH$_3$).

(d) Synthesis of estra-1,3,5(10)-trien-17-ono-[3,2,e]-1',2',3'-oxathiazine-2'2'-dioxide (6):

To a solution of chlorosulfonyl isocyanate (4.3 mL, 50 mmol) in CH$_2$Cl$_2$ (25 mL) was added formic acid (10 mL of a CH$_2$Cl$_2$ solution, 5.0M, 50 mmol) at 0° C. The reaction mixture was warmed to room temperature and stirred for 1 h. To a solution of 3-hydroxyestra-1,3,5(10)-trien-17-one-2-carboxaldehyde (5, 2.98 g, 10 mmol) in DMF (120 mL) was added sodium hydride (2.00 g of a mineral oil dispersion, 60%, 50 mmol) at 0° C. The reaction mixture was stirred for 1 h, the pre-prepared reagent was added, and stirring continued for 4 h. The reaction mixture was quenched with saturated aqueous NH$_4$Cl at 0° C., then extracted with EtOAc. The combined organic layers were washed with H$_2$O, then with saturated aqueous NaCl, and dried (Na₂SO₄). The desiccant was filtered and the solvent was evaporated at reduced pressure. The residue was purified by column chromatography (silica gel) using CHCl₃:EtOAc (20:1→10:1, v/v) to afford 0.696 g of the starting material 5 (23% yield) and 1.88 g of 6 (52% yield), m.p. >250° C.

¹H NMR: δ 8.63 (s, 1H, —CH═N—), 7.59 (s, 1H, aromatic), 7.06 (s, 1H, aromatic), 0.98 (s, 3H, 18-CH₃); MS (EI): m/z 359 (M⁺). HRMS calcd. for C₁₉H₂₀N₁O₄S₁, 358.1113; found, 358.1140.

EXAMPLE 3

Preparation of 17β-Hydroxyestra-1,3,5(10)-trieno-[3,2,e]-1',2',3'-oxathiazine-2',2'-dioxide (10)

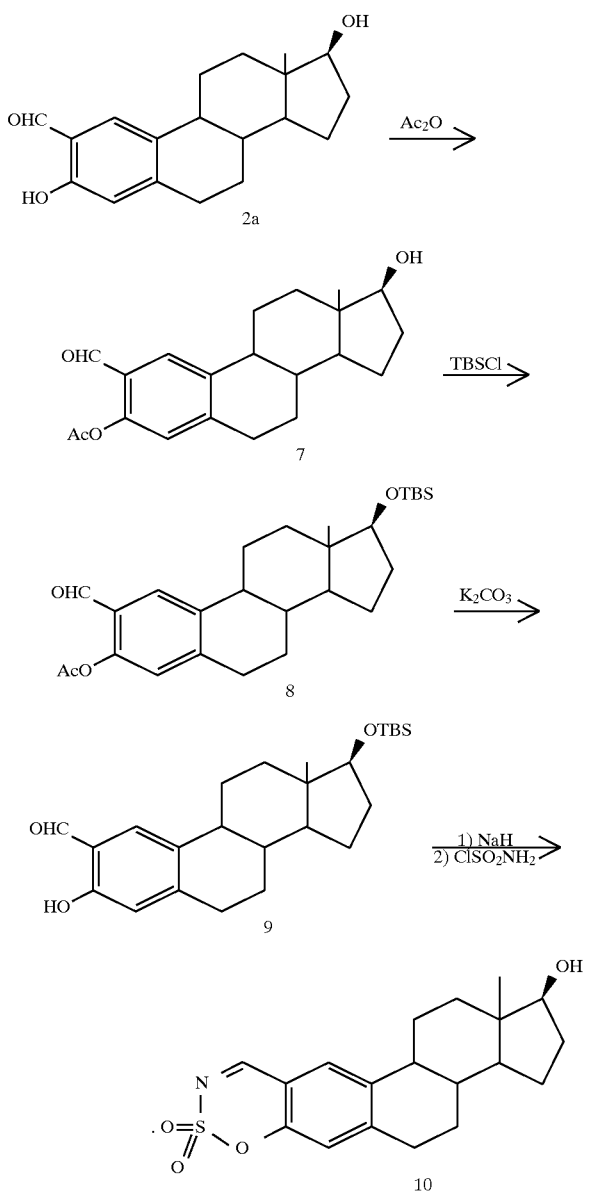

Scheme 3

(a) Synthesis of 3,17β-dihydroxyestra-1,3,5(10)-triene-2-carboxaldehyde 3-acetate (7):

To a solution of 3,17β-dihydroxyestra-1,3,5(10)-triene-2-carboxaldehyde (2a, 0.300 g, 1.0 mmol) in THF (10 mL) and CH₂Cl₂ (6.0 mL) were added triethylamine (0.34 mL, 2.5 mmol) and acetic anhydride (0.14 mL, 1.5 mmol) at room temperature. The reaction mixture was stirred for 18 h, H₂O added, and the mixture extracted with EtOAc. The combined organic layers were washed with H₂O, then with saturated aqueous NaCl, and dried (MgSO₄). The desiccant was filtered and the solvent was evaporated at reduced pressure. The residue was purified by column chromatography (silica gel) using n-hexane:EtOAc (3:2, v/v) to afford 0.336 g of 7 (98% yield), m.p. 73°–75° C.

¹H NMR: δ 7.83 (s, 1H, aromatic), 6.91 (s, 1H, aromatic), 3.78 (t, 1H, 17α-H), 2.42 (s, 3H, —OCOCH₃), 0.83 (s, 3H, 18-CH₃).

(b) Synthesis of 17β-tert-butyldimethylsilyloxy-3-hydroxyestra-1,3,5(10)-triene-2-carboxaldehyde 3-acetate (8):

To a solution of 3,17β-dihydroxyestra-1,3,5(10)-triene-2-carboxaldehyde 3-acetate (7, 0.330 g, 0.97 mmol) in DMF (2.0 mL) were added imidazole (0.131 g, 1.9 mmol) and tert-butyldimethylchlorosilane (0.218 g, 1.5 mmol) at room temperature. The reaction mixture was stirred for 2 h, diluted with EtOAc, washed with H₂O, then with saturated aqueous NaCl, and dried (MgSO₄). The desiccant was filtered and the solvent was evaporated at reduced pressure. The residue was purified by column chromatography (silica gel) using n-hexane:EtOAc (10:1→3:1, v/v) to afford 0.195 g of 8 (44% yield).

¹H NMR: δ 9.98 (s, 1H, —CHO), 7.74 (s, 1H, aromatic), 6.83 (s, 1H, aromatic), 3.62 (t, 1H, 17α-H), 2.34 (s, 3H, —OCOCH₃), 0.87 (s, 9H, —C(CH₃)₃), 0.72 (s, 3H, 18-CH₃), 0.01 and 0.00 (s, each 3H, —Si(CH₃)₂).

(c) Synthesis of 17β-tert-butyldimethylsilyloxy-3-hydroxyestra-1,3,5(10)-triene-2-carboxaldehyde (9):

To a solution of 17β-tert-butyldimethylsilyloxy-3-hydroxyestra-1,3,5(10)-triene-2-carboxaldehyde 3-acetate (8, 0.190 g, 0.42 mmol) in MeOH (3.0 mL) was added potassium carbonate (0.058 g, 0.42 mmol) at 0° C. The reaction mixture was stirred for 1 h, diluted with EtOAc, washed with H₂O, then with saturated aqueous NaCl, and dried (MgSO₄). The desiccant was filtered and the solvent was evaporated at reduced pressure. The residue was purified by column chromatography (silica gel) using n-hexane:EtOAc (10:1, v/v) to afford 0.135 g of 9 (81% yield).

¹H NMR: δ 10.74 (s, 1H, —OH), 9.79 (s, 1H, —CHO), 7.39 (s, 1H, aromatic), 6.66 (s, 1H, aromatic), 3.62 (t, 1H, 17α-H), 0.87 (s, 9H, —C(CH₃)₃), 0.72 (s, 3H, 18-CH₃), 0.01 and 0.00 (s, each 3H, —Si(CH₃)₂).

(d) Synthesis of 17β-hydroxyestra-1,3,5(10)-trieno-[3,2,e]-1',2',3'-oxathiazine-2',2'-dioxide (10):

To a solution of chlorosulfonyl isocyanate (0.13 mL, 1.5 mmol) in CH₂Cl₂ (1.0 mL) was added formic acid (0.31 mL of a CH₂Cl₂ solution, 5.0M, 1.6 mmol) at 0° C. The reaction mixture was warmed to room temperature and stirred for 1 h. To a solution of 17β-tert-butyldimethylsilyloxy-3-hydroxyestra-1,3,5(10)-triene-2-carbox aldehyde (9, 0.129 g, 0.31 mmol) in DMF (3.0 mL) was added sodium hydride (0.044 g of a mineral oil dispersion, 60%, 1.1 mmol) at 0° C. The reaction mixture was stirred for 1 h, the pre-prepared reagent was added, and stirring continued for 4 h at room temperature. The reaction mixture was quenched with saturated aqueous NH₄Cl at 0° C. and extracted with EtOAc. The combined organic layers were washed with H₂O, then with saturated aqueous NaCl, and dried (MgSO₄). The desiccant was filtered and the solvent was evaporated at reduced pressure. The residue was purified by column chromatography (silica gel) using n-hexane:acetone (2:1→1:1, v/v) to afford 0.017 g of 2a (18% yield) and 0.030 g of 10 (27% yield), m.p. 170°–172° C.

$^1$H NMR: δ 8.62 (s, 1H, —CH=N—), 7.58 (s, 1H, aromatic), 7.03 (s, 1H, aromatic), 3.78 (t, 1H, 17α-H), 0.84 (s, 3H, 18-CH$_3$); MS (EI): m/z 361 (M$^+$). HRMS calcd. for C$_{19}$H$_{24}$N$_1$O$_4$S$_1$, 362.1426; found 362.1448.

EXAMPLE 4

Preparation of 17β-Hydroxyestra-1,3,5(10)-trieno-[3,2,e]-3',4'-dihydro-1',2',3'-oxathiazine-2',2'-dioxide (11)

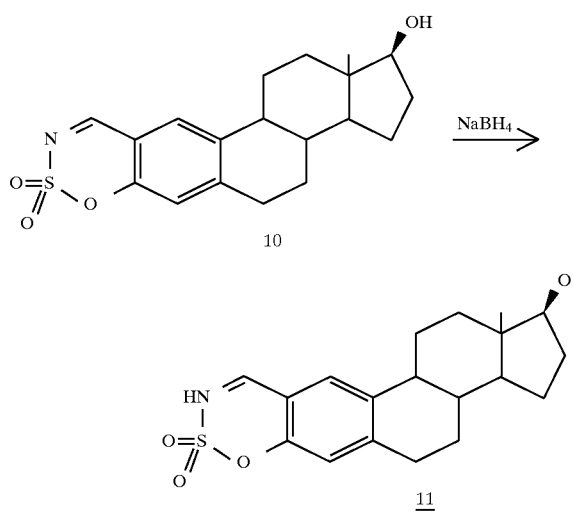

To a solution of 17β-hydroxyestra-1,3,5(10)-trieno-[3,2,e]-1',2',3'-oxathiazine-2',2'-dioxide (10, 0.024 g, 0.067 mmol) in MeOH (2.0 mL) was added sodium borohydride (0.005 g, 0.13 mmol) at 0° C. The reaction mixture was stirred for 30 min, quenched with saturated aqueous NH$_4$Cl at 0° C., and extracted with EtOAc. The combined organic layers were washed with H$_2$O, then with saturated aqueous NaCl, and dried (MgSO$_4$). The desiccant was filtered and the solvent was evaporated at reduced pressure. The residue was purified by column chromatography (silica gel) using CHCl$_3$:MeOH (20:1, v/v) to afford 0.019 g of 11 (80% yield), m.p. 231°–232° C.

$^1$H NMR (CDCl$_3$-CD$_3$OD): δ 6.94 (s, 1H, aromatic), 6.64 (s, 1H, aromatic), 4.49 (s, 2H, —CH$_2$N—), 3.64 (t, 1H, 17α-H), 0.74 (s, 3H, 18-CH$_3$); MS (EI): m/z 363 (M$^+$). HRMS calcd. for C$_{19}$H$_{25}$N$_1$O$_4$S$_1$, 362.1426; found, 362.1449.

EXAMPLE 5

Preparation of Estra-1,3,5(10)-trien-17-ono-[3,4,e]-1',2',3'-oxathiazine-2',2'-dioxide (13)

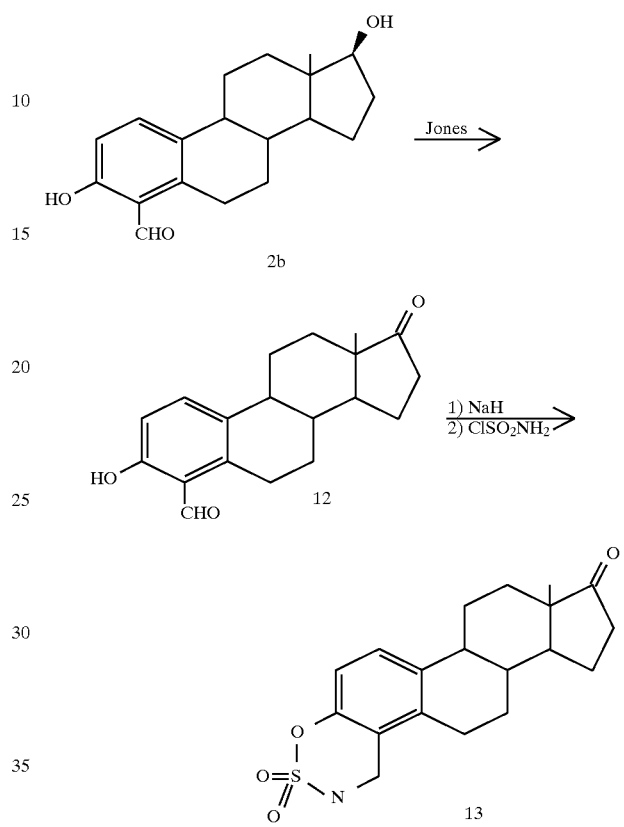

(a) Synthesis of 3-hydroxyestra-1,3,5(10)-trien-17-one-4-carboxaldehyde (12):

To a solution of 3,17β-dihydroxyestra-1,3,5(10)-triene-4-carboxaldehyde (2b, 0.300 g, 1.0 mmol) in acetone (10 mL) was added Jones reagent (0.50 mL) at 0° C. The reaction mixture was stirred for 10 min, quenched with 2-propanol, and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:THF (4:1→2:1, v/v) to afford 0.276 g of 12 (93% yield), m.p. 234°–237° C.

$^1$H NMR: δ 12.04 (s, 1H, —OH), 10.44 (s, 1H, —CHO), 7.53 (d, 1H, aromatic), 6.85 (d, 1H, aromatic), 0.97 (s, 3H, 18-CH$_3$).

(b) Synthesis of estra-1,3,5(10)-trien-17-ono-[3,4,e]-1',2',3'-oxathiazine-2',2'-dioxide (13):

To a solution of chlorosulfonyl isocyanate (0.30 mL, 3.5 mmol) in CH$_2$Cl$_2$ (2.0 mL) was added formic acid (0.70 mL of a CH$_2$Cl$_2$ solution, 5.0M, 3.5 mmol) at 0° C. The reaction mixture was warmed to room temperature and stirred for 1 h. To a solution of 3-hydroxyestra-1,3,5(10)-trien-17-one-4-carboxaldehyde (12, 0.207 g, 0.69 mmol) in DMF (10 mL) was added sodium hydride (0.140 g of a mineral oil dispersion, 60%, 3.5 mmol) at 0° C. The reaction mixture was stirred for 1 h, the pre-prepared reagent was added, and stirring continued for 3 h at room temperature. The reaction mixture was quenched with saturated aqueous NH₄Cl at 0° C., and extracted with EtOAc. The combined organic layers were washed with H₂O, then with saturated aqueous NaCl, and dried (Na₂SO₄). The desiccant was filtered and the solvent was evaporated at reduced pressure. The residue was purified by column chromatography (silica gel) using n-hexane:THF (3:1→2:1, v/v) to afford 0.069 g of 12 (34% yield) and 0.090 g of 13 (37% yield), m.p. 94°–96° C.

¹H NMR: δ 9.00 (s, 1H, —CH═N—), 7.72 (d, 1H, aromatic), 7.13 (d, 1H, aromatic), 0.97 (s, 3H, 18-CH₃); MS (EI): m/z 359 (M⁺). HRMS calcd. for $C_{19}H_{20}N_1O_4S_1$, 358.1113; found, 358.1128.

EXAMPLE 6

Preparation of 17β-Hydroxyestra-1,3,5(10)-trieno-[3,4,e]-3',4'-dihydro-1',2',3'-oxathiazine-2',2'-dioxide (14)

Scheme 6

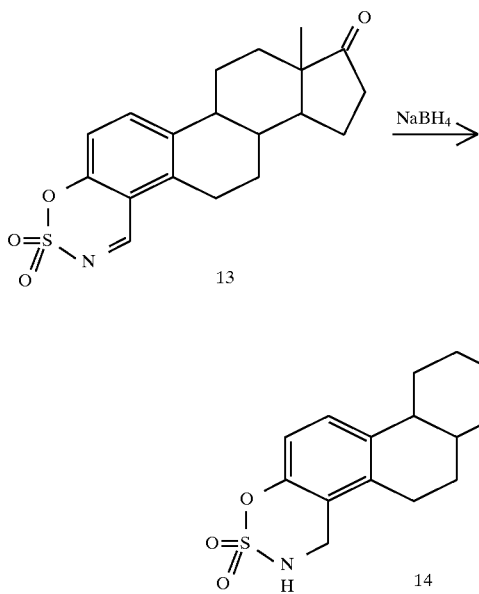

To a solution of estra-1,3,5(10)-trien-17-ono-[3,4,e]-1',2',3'-oxathiazine-2',2'-dioxide (13, 0.036 g, 0.10 mmol) in MeOH (2.0 mL) was added sodium borohydride (0.006 g, 0.16 mmol) at 0° C. The reaction mixture was stirred for 30 min, and quenched with saturated aqueous NH₄Cl at 0° C., and extracted with EtOAc. The combined organic layers were washed with H₂O, then with saturated aqueous NaCl, and dried (Na₂SO₄). The desiccant was filtered and the solvent was evaporated at reduced pressure. The residue was purified by column chromatography (silica gel) using CHCl₃:acetone (5:1→3:1, v/v) to afford 0.024 g of 14 (67% yield), m.p. >250° C.

¹H NMR (CDCl₃-CD₃OD): δ 7.26 (d, 1H, aromatic), 6.80 (d, 1H, aromatic), 4.44 (AB type, 2H, —CH₂N—), 3.69 (t, 1H, 17α-H), 0.76 (s, 3H, 18-CH₃); MS (EI): m/z 363 (M⁺). HRMS calcd. for $C_{19}H_{25}N_1O_4S_1$, 363.1504; found, 363.1529.

EXAMPLE 7

Preparation of 19-Norpregna-1,3,5(10)-trieno-[3,2,e]-1',2',3'-oxathiazine-2',2'-dioxide (17)

Scheme 7

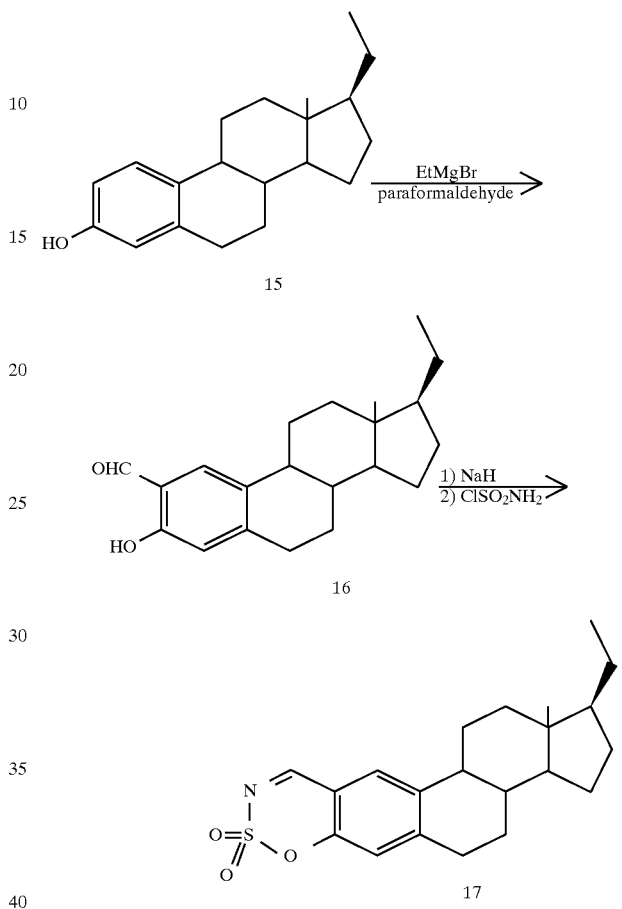

(a) Synthesis of 3-hydroxy-19-norpregna-1,3,5(10)-triene-2-carboxaldehyde (16):

To a suspension of magnesium (0.243 g, 10 mmol) in THF (2.0 mL) was added bromoethane (0.90 mL, 12 mmol), dissolved in THF (2.0 mL) at room temperature. 19-Norpregna-1,3,5(10)-trien-3-ol (15, 0.569 g, 2.0 mmol; synthesized by the method of Peters et al., J. Med. Chem. 32(7):1642 (1989)) dissolved in THF (5.0 mL) was added to the reaction mixture, and stirring continued for 30 min. The solvent was removed at reduced pressure, and to the residue were added benzene (23 mL), hexamethylphosphoric triamide (0.9 mL, 5.0 mmol) and paraformaldehyde (0.420 g). Stirring was continued for 3 h at 80° C. After the reaction mixture was cooled to room temperature, 5N HCl (10 mL) was added and the mixture extracted with EtOAc. The combined organic layers were washed with H₂O, then with saturated aqueous NaCl, and dried (Na₂SO₄). The desiccant was filtered and the solvent was evaporated at reduced pressure. The residue was purified by column chromatography (silica gel) using n-hexane:CHCl₃ (2:1→1:1, v/v) to afford 0.493 g of 16 (80% yield), m.p. 126°–127° C.

¹H NMR: δ 10.77 (s, 1H, —OH), 9.81 (s, 1H, —CHO), 7.42 (s, 1H, aromatic), 6.69 (s, 1H, aromatic), 0.91 (t, 3H, 21-CH₃), 0.62 (s, 3H, 18-CH₃); MS (EI): m/z 312(M⁺).

(b) Synthesis of 19-norpregna-1,3,5(10)-trieno-[3,2,e]-1',2',3'-oxathiazine-2',2'-dioxide (17):

To a solution of chlorosulfonyl isocyanate (0.26 mL, 3.0 mmol) in CH$_2$Cl$_2$ (1.0 mL) was added formic acid (0.60 mL of a CH$_2$Cl$_2$ solution, 5.0M, 3.0 mmol) at 0° C. The reaction mixture was warmed to room temperature and stirred for 1 h. To a solution of 3-hydroxy-19-norpregna-1,3,5(10)-triene-2-carboxaldehyde (16, 0.187 g, 0.6 mmol) in DMF (3.0 mL) and THF (2.0 mL) was added sodium hydride (0.120 g of a mineral oil dispersion, 60%, 3.0 mmol) at 0° C. The reaction mixture was stirred for 1 h, the pre-prepared reagent was added, and stirring continued for 1 h at 0° C. and additional 16 h at room temperature. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:CHCl$_3$ (1:1, v/v) hexane:CHCl$_3$:EtOAc (5:5:1, v/v) to afford 0.089 g of 16 (47% yield) and 0.069 g of 17 (31% yield), m.p. 173°–174° C.

$^1$H NMR: d 8.58 (s, 1H, —CH=N—), 7.53 (s, 1H, aromatic), 6.98 (s, 1H, aromatic), 0.91 (t, 3H, 21-CH$_3$), 0.62 (s, 3H, 18-CH$_3$); MS (EI): m/z 373(M$^+$). HRMS calcd. for C$_{21}$H$_{28}$N$_1$O$_3$S$_1$, 374.1790; found, 374.1806.

The following scheme illustrates the synthetic steps carried out in Examples 8 through 14 to make the enzyme inhibitors (30), (31), (32), (33), (34), (35) and (36):

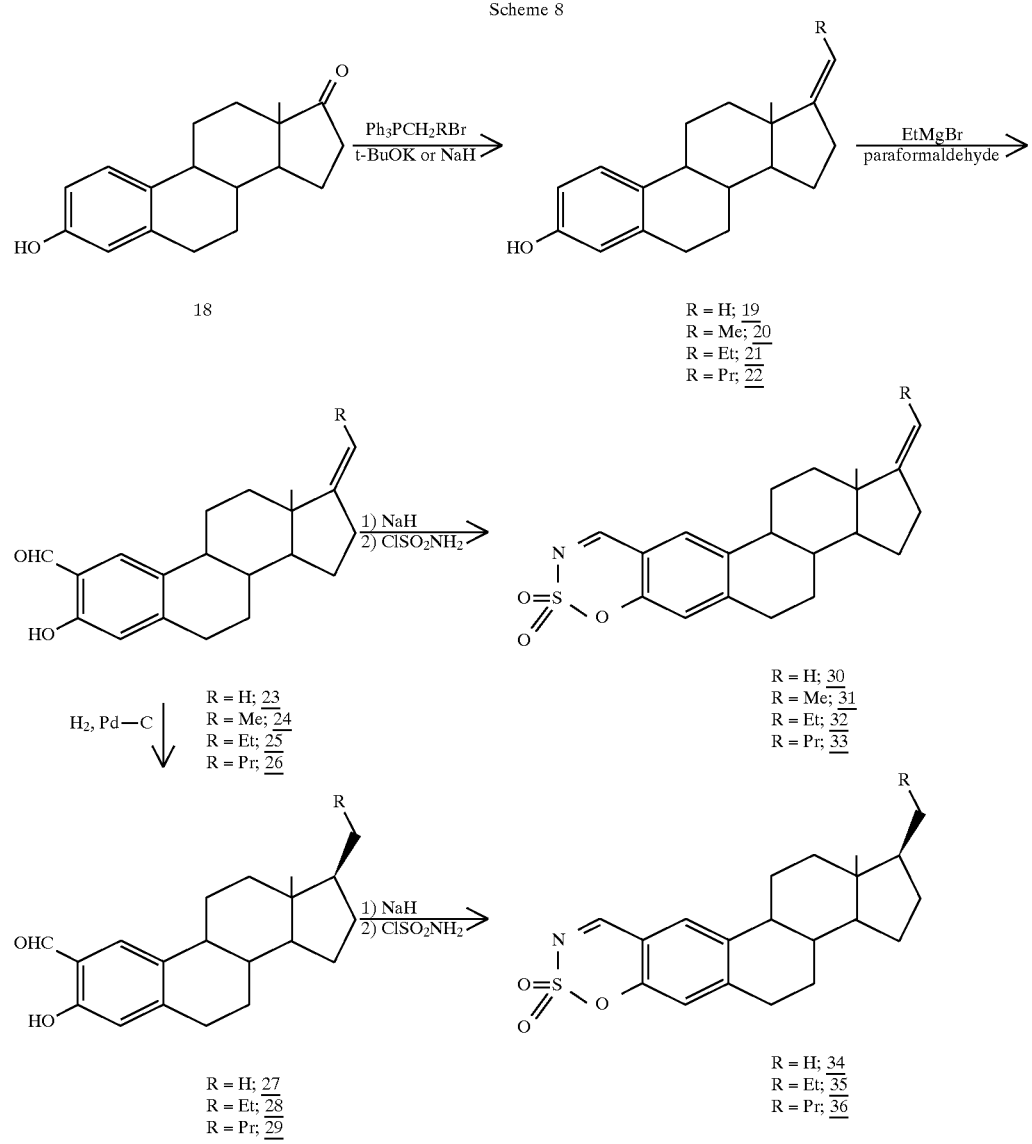

Scheme 8

EXAMPLE 8

Preparation of 17-Methyleneestra-1,3,5(10)-trieno-[3,2,e]-1',2',3'-oxathiazine-2',2'-dioxide (30)

(a) Synthesis of 17-methyleneestra-1,3,5(10)-trien-3-ol (19):

To a suspension of methyl triphenylphosphonium bromide (8.93 g, 25.0 mmol) in THF (120 mL) was added potassium tert-butoxide (2.69 g, 24 mmol) and stirred for 30 min at room temperature. The reaction mixture was added estrone (18, 2.70 g, 10 mmol), stirred for 19 h at room temperature. The reaction mixture was quenched with saturated aqueous NH₄Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (5:1→3:1, v/v) to afford 2.24 g of 19 (84% yield), m.p. 135°–136° C.

$^1$H NMR: δ 7.17 (d, 1H, aromatic), 6.68–6.52 (m, 2H, aromatic), 4.73–4.55 (m, 3H, —OH, =CH$_2$), 0.82 (s, 3H, 18-CH$_3$).

(b) Preparation of [17(20)Z]-19-norpregna-1,3,5(10),17(20)-tetraen-3-ol (20):

To a suspension of ethyl triphenylphosphonium bromide (4.64 g, 12.5 mmol) in THF (40 mL) was added potassium tert-butoxide (1.35 g, 12 mmol) and stirred for 30 min at room temperature. The reaction mixture was added estrone (18, 1.35 g, 5.0 mmol), stirred for 24 h at room temperature. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (5:1→2:1, v/v) to afford 1.03 g of 20 (72% yield), m.p. 138°–139° C.

$^1$H NMR: δ 7.16 (d, 1H, aromatic), 6.68–6.50 (m, 2H, aromatic), 5.22–5.08 (m, 1H, =CH—CH$_3$), 4.48 (s, 1H, —OH), 1.72–1.65 (m, 3H, =CH—CH$_3$), 0.91 (s, 3H, 18-CH$_3$).

(c) Preparation of [17(20)Z]-propylideneestra-1,3,5(10)-trien-3-ol (21):

To sodium hydride (1.20 g of a mineral oil dispersion, 60%, 30.0 mmol) was added DMSO (100 mL) and the mixture stirred for 1 h at 75° C. To the reaction mixture was added propyl triphenylphosphonium bromide (12.3 g, 32.0 mmol), and stirring continued for 30 min at room temperature. To the reaction mixture was added estrone (18, 2.70 g, 10 mmol), stirred for 4 days at 80° C. The reaction mixture was quenched with saturated aqueous NH$_4$Cl at 0° C. and extracted with Et$_2$O. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (10:1→1:1, v/v) to afford 1.30 g of 21 (44% yield) and 1.05 g of 18 (39% yield), m.p. 149°–151° C.

$^1$H NMR: δ 7.15 (d, 1H, aromatic), 6.68–6.50 (m, 2H, aromatic), 5.12–5.00 (m, 1H, =CH—CH$_2$—), 4.57 (s, 1H, —OH), 0.96 (t, 3H, 23-CH$_3$), 0.90 (s, 3H, 18-CH$_3$).

(d) Preparation of [17(20)Z]-19,21-dinorchola-1,3,5(10)17(20)-tetraen-3-ol (22):

To a suspension of butyl triphenylphosphonium bromide (12.8 g, 32.0 mmol) in THF (100 mL) was added potassium tert-butoxide (3.37 g, 30 mmol) and stirred for 30 min at room temperature. To the reaction mixture was added estrone (18, 2.70 g, 10 mmol), and stirring continued for 5 days at 80° C. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (10:1→2:1, v/v) to afford 2.45 g of 22 (79% yield), m.p. 85°–86° C.

$^1$H NMR: δ 7.15 (d, 1H, aromatic), 6.70–6.52 (m, 2H, aromatic), 5.13–5.00 (m, 1H, =CH—CH$_2$—), 4.49 (s, 1H, —OH), 0.91 (t, 3H, 24-CH$_3$),0.90 (s, 3H, 18-CH$_3$).

(e) Preparation of 3-hydroxy-17-methyleneestra-1,3,5(10)-triene-2-carboxaldehyde (23):

To a suspension of magnesium (0.365 g, 15 mmol) in THF (3.0 mL) was added bromoethane (1.5 mL, 20 mmol) dissolved in THF (3.0 mL) at room temperature. 17-Methyleneestra-1,3,5(10)-trien-3-ol (19, 0.805 g, 3.0 mmol) dissolved in THF (7.5 mL) was added to the reaction mixture, and stirring continued for 30 min. The solvent was removed at reduced pressure, and to the residue were added benzene (35 mL), hexamethylphosphoric triamide (1.4 mL, 7.5 mmol) and paraformaldehyde (0.630 g). Stirring was continued for 6 h at 80° C. After the reaction mixture was cooled to room temperature, 5N HCl (15 mL) was added and the mixture extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:AcOEt (10:1→3:1, v/v) to afford 0.695 g of 23 (78% yield), m.p. 128°–130° C.

$^1$H NMR: δ 10.78 (s, 1H, —OH), 9.82 (s, 1H, —CHO), 7.44 (s, 1H, aromatic), 6.70 (s, 1H, aromatic), 4.85–4.58 (m, 2H, =CH$_2$), 0.84 (s, 3H, 18-CH$_3$).

(f) Preparation of 17-methyleneestra-1,3,5(10)-trieno-[3,2,e]-1',2',3'-oxathiazine-2',2'-dioxide (30):

To a solution of chlorosulfonyl isocyanate (0.43 mL, 5.0 mmol) in CH$_2$Cl$_2$ (2.0 mL) was added formic acid (1.0 mL of a CH$_2$Cl$_2$ solution, 5.0M, 5.0 mmol) at 0° C. The reaction mixture was warmed to room temperature and stirred for 1 h. To a solution of 3-hydroxy-17-methyleneestra-1,3,5(10)-triene-2-carboxaldehyde (23, 0.267 g, 0.9 mmol) in DMF (5.0 mL) was added sodium hydride (0.200 g of a mineral oil dispersion, 60%, 5.0 mmol) at 0° C. The reaction mixture was stirred for 1 h, the pre-prepared reagent was added, and stirring continued for 2 h at 0° C. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (10:1, v/v)→CHCl$_3$:EtOAc (20:1, v/v) to afford 0.254 g of 30 (79% yield), m.p. 176°–179° C.

$^1$H NMR: δ 8.59 (s, 1H, —CH=N—), 7.55 (s, 1H, aromatic), 6.99 (s, 1H, aromatic), 4.78–4.63 (m, 2H, =CH$_2$), 0.84 (s, 3H, 18-CH$_3$); MS (DCI): m/z 375 (M$^+$+NH$_4$), 358 (M$^+$+H). HRMS calcd. for C$_{20}$H$_{24}$N$_1$O$_3$S$_1$, 358.1477; found, 358.1486.

EXAMPLE 9

Preparation of [17(20)Z]-Norpregna-1,3,5(10),17(20)-tetraeno-[3,2,e]-1',2',3'-oxathiazine-2',2'-dioxide (31)

(a) 3-Hydroxy-[17(20)Z]-19-norpregna-1,3,5(10),17(20)-tetraene-2-carboxaldehyde (24):

Using the procedure of Example 8, part (e), there was obtained from [17(20)Z]-19-norpregna-1,3,5(10),17(20)-tetraen-3-ol (20, 0.480 g, 1.7 mmol) after chromatography (n-hexane:AcOEt, 30:1→10:1, v/v), 0.495 g of 24 (94% yield), m.p. 107°–109° C.

$^1$H NMR: δ 10.78 (S, 1H, —OH), 9.82 (s, 1H, —CHO), 7.42 (s, 1H, aromatic), 6.70 (s, 1H, aromatic), 5.34–5.06 (m, 1H, =C$\underline{H}$—CH$_3$), 1.78–1.66 (m, 3H, =CH—C$\underline{H}_3$), 0.92 (s, 3H, 18-CH$_3$); MS (EI): m/z 310 (M$^+$).

(b) Preparation of [17(20)Z]-norpregna-1,3,5(10),17(20)-tetraeno-[3,2,e]-1',2',3'-oxathiazine-2',2'-dioxide (31):

Using the procedure of Example 8, part (f), there was obtained from 3-hydroxy-[17(20)Z]-norpregna-1,3,5(10),17(20)-tetraene-2-carboxaldehyde (24, 0.310 g, 1.0 mmol) after chromatography (n-hexane:CHCl$_3$:EtOAc, 15:15:1, v/v) 0.276 g of 31 (74% yield), m.p. 185°–186° C.

$^1$H NMR: δ 8.59 (s, 1H, —CH=N—), 7.53 (s, 1H, aromatic), 6.99 (s, 1H, aromatic), 5.25–5.05 (m, 1H, =C$\underline{H}$—CH$_3$), 1.75–1.65 (m, 3H, =CH—C$\underline{H}_3$), 0.92 (s, 3H, 18-CH$_3$); MS (DCI): m/z 389 (M$^+$+NH$_4$), 372 (M$^+$+H). HRMS calcd. for C$_{21}$H$_{26}$N$_1$O$_3$S$_1$, 372.1633; found, 372.1656.

EXAMPLE 10

Preparation of [17(20)Z]-Norpregna-1,3,5(10),17(20)-tetraeno-[3,2,e]-1',2',3'-oxathiazine-2',2'-dioxide (32)

(a) Preparation of 3-hydroxy-[17(20)Z]-propylideneestra-1,3,5(10)-triene-2-carboxaldehyde (25):

Using the procedure of Example 8, part (e), there was obtained from [17(20)Z]-propylideneestra-1,3,5(10)-trien-3-ol (21, 1.03 g, 3.5 mmol) after chromatography (n-hexane:AcOEt, 30:1→10:1, v/v), 0.983 g of 25 (87% yield).

$^1$H NMR: δ 10.77 (s, 1H, —OH), 9.82 (s, 1H, —CHO), 7.42 (s, 1H, aromatic), 6.70 (s, 1H, aromatic), 5.13–4.98 (m, 1H, =C$\underline{H}$—CH$_2$—), 0.97 (t, 3H, 23-CH$_3$), 0.92 (s, 3H, 18-CH$_3$); MS (EI): m/z 324 (M$^+$).

(b) Preparation of [17(20)Z]-Propylideneestra-1,3,5(10)-trieno-[3,2,e]-1',2',3'-oxathiazine-2',2'-dioxide (32):

Using the procedure of Example 8, part (f), there was obtained from 3-hydroxy-[17(20)Z]-propylideneestra-1,3,5(10)-triene-2-carboxaldehyde (25, 0.195 g, 0.6 mmol) after chromatography (n-hexane:EtOAc, 15:1→10:1, v/v) 0.163 g of 32 (71% yield), m.p. 140°–142° C.

$^1$H NMR: δ 8.58 (s, 1H, —CH=N—), 7.53 (s, 1H, aromatic), 6.99 (s, 1H, aromatic), 5.22–5.00 (m, 1H, =C$\underline{H}$—CH$_2$—), 0.97 (t, 3H, 23-CH$_3$), 0.92 (s, 3H, 18-CH$_3$); MS (EI): m/z 385 (M$^+$). HRMS calcd. for C$_{22}$H$_{28}$N$_1$O$_3$S$_1$, 386.1790; found, 386.1795.

EXAMPLE 11

Preparation of [17(20)Z]-19,21-Dinorchola-1,3,5(10),17(20)-tetraeno-[3,2,e]-1',2',3'-oxathiazine-2',2'-dioxide (33)

(a) Preparation of 3-hydroxy-[17(20)Z]-19,21-dinorchola-1,3,5(10),17(20)-tetraene-2-carboxaldehyde (26):

Using the procedures of Example 8, part (e), there was obtained from [17(20)Z]-19,21-dinorchola-1,3,5(10),17(20)-tetraen-3-ol (22, 1.24 g, 4.0 mmol) after chromatography (n-hexane:AcOEt, 30:1→5:1, v/v) 1.19 g of 26 (88% yield).

$^1$H NMR: δ 10.79 (s, 1H, —OH), 9.83 (s, 1H, —CHO), 7.43 (s, 1H, aromatic), 6.71 (s, 1H, aromatic), 5.17–5.02 (m, 1H, =C$\underline{H}$—CH$_2$—), 0.93 (t, 3H, 24-CH$_3$), 0.93 (s, 3H, 18-CH$_3$); MS (EI): m/z 338 (M$^+$).

(b) Preparation of [17(20)Z]-19,21-dinorchola-1,3,5(10),17(20)-tetraeno-[3,2,e]-1',2',3'-oxathiazine-2',2'-dioxide (33):

Using the procedures of Example 8, part (f), there was obtained from 3-hydroxy-[17(20)Z]-19,21-dinorchola-1,3,5(10),17(20)-tetraene-2-carboxaldehyde (26, 0.169 g, 0.5 mmol) after chromatography (n-hexane:EtOAc, 20:1→5:1, v/v) 0.107 g of 33 (53% yield), m.p. 163° C.

$^1$H NMR: δ 8.58 (s, 1H, —CH=N—), 7.53 (s, 1H, aromatic), 6.99 (s, 1H, aromatic), 5.15–5.00 (m, 1H, =C$\underline{H}$—CH$_2$—), 0.92 (t, 3H, 24-CH$_3$), 0.92 (s, 3H, 18-CH$_3$); MS (EI): m/z 399 (M$^+$). HRMS calcd. for C$_{23}$H$_{30}$N$_1$O$_3$S$_1$, 400.1946; found, 400.1925.

EXAMPLE 12

Preparation of 17β-Methylestra-1,3,5(10)-trieno-[3,2,e]-1',2',3'-oxathiazine-2',2'-dioxide (34)

(a) Synthesis of 3-hydroxy-17β-methylestra-1,3,5(10)-triene-2-carboxaldehyde (27):

To a solution of 3-hydroxy-17-methyleneestra-1,3,5(10)-triene-2-carboxaldehyde (23, 0.401 g, 1.35 mmol) in EtOAc (10 mL) was added 10% palladium on carbon (0.060 g). The reaction mixture was stirred for 4 h under the hydrogen atmosphere at room temperature. After the catalyst was filtered, the solvent was evaporated at reduced pressure. The residue was purified by column chromatography (silica gel) using n-hexane:EtOAc (10:1→2:1, v/v) to afford 0.307 g of 27 (76% yield).

$^1$H NMR: δ 10.77 (s, 1H, —OH), 9.82 (s, 1H, —CHO), 7.43 (s, 1H, aromatic), 6.70 (s, 1H, aromatic), 0.88 (d, 3H, 20-CH$_3$), 0.60 (s, 3H, 18-CH$_3$).

(b) Synthesis of 17β-methylestra-1,3,5(10)-trieno-[3,2,e]-1',2',3'-oxathiazine-2',2'-dioxide (34):

By the procedure described in Example 8, part (f), there was obtained from 3-hydroxy-17β-methylestra-1,3,5(10)-triene-2-carboxaldehyde (27, 0.298 g, 1.0 mmol) after chromatography (n-hexane:EtOAc, 10:1→5:1, v/v) 0.181 g of 34 (50% yield), m.p. 194°–196° C.

$^1$H NMR: δ 8.58 (s, 1H, —CH=N—), 7.54 (s, 1H, aromatic), 6.98 (s, 1H, aromatic), 0.89 (d, 3H, 20-CH$_3$), 0.60 (s, 3H, 18-CH$_3$); MS (DCI): m/z 377 (M$^+$+NH$_4$), 360 (M$^+$+H). HRMS calcd. for C$_{20}$H$_{26}$N$_1$O$_3$S$_1$, 360.1633; found, 360.1657.

EXAMPLE 13

Preparation of 17β-Propylestra-1,3,5(10)-trieno-[3,2,e]-1',2',3'-oxathiazine-2',2'-dioxide (35)

(a) Synthesis of 3-hydroxy-17β-propylestra-1,3,5(10)-triene-2-carboxaldehyde (28): Using the procedure of Example 12, part (a), there was obtained from 3-hydroxy-[17(20)Z]-propylideneestra-1,3,5(10)-triene-2-carboxaldehyde (25, 0.714 g, 2.20 mmol) after chromatography (n-hexane:AcOEt, 30:1→10:1, v/v) 0.489 g of 28 (68% yield), m.p. 122°–123° C.

$^1$H NMR: δ 10.77 (s, 1H, —OH), 9.81 (s, 1H, —CHO), 7.42 (s, 1H, aromatic), 6.69 (s, 1H, aromatic), 0.91 (t, 3H, 23-CH$_3$), 0.62 (s, 3H, 18-CH$_3$); MS (EI): m/z 326 (M$^+$).

(b) Preparation of 17β-propylestra-1,3,5(10)-trieno-[3,2,e]-1',2',3'-oxathiazine-2',2'-dioxide (36):

Using the procedure in Example 8, part (f), there was obtained from 3-hydroxy-17β-propylestra-1,3,5(10)-triene-2-carboxaldehyde (28, 0.196 g, 0.6 mmol) after chromatography (n-hexane:EtOAc, 15:1→10:1, v/v) 0.206 g of 35 (89% yield), m.p. 167°–169° C.

$^1$H NMR: δ 8.57 (s, 1H, —CH=N—), 7.53 (s, 1H, aromatic), 6.98 (s, 1H, aromatic), 0.92 (t, 3H, 23-CH$_3$), 0.62

(s, 3H, 18-CH$_3$); MS (EI): m/z 387 (M$^+$). HRMS calcd. for C$_{22}$H$_{30}$N$_1$O$_3$S$_1$, 388.1946; found, 388.1967.

EXAMPLE 14

Preparation of 17β-Propylestra-1,3,5(10)-trieno-[3,2,e]-1',2',3'-oxathiazine-2',2'-dioxide (36)

(a) Synthesis of 3-hydroxy-17β-19,21-dinorchola-1,3,5 (10)-triene-2-carboxaldehyde (29):

Using the procedure of Example 12, part (a), there was obtained from 3-hydroxy-[17(20)Z]-19,21-dinorchola-1,3,5 (10),17(20)-tetraene-2-carboxaldehyde (26, 0.580g, 1.71 mmol) after chromatography (n-hexane:AcOEt, 30:1→1:1, v/v) 0.341 g of 29 (59% yield). m.p. 102°–103° C.

$^1$H NMR: δ 10.77 (s, 1H, —OH), 9.81 (s, 1H, —CHO), 7.42 (s, 1H, aromatic), 6.69 (s, 1H, aromatic), 0.90 (t, 3H, 24-CH$_3$), 0.62 (s, 3H, 18-CH$_3$); MS (EI): m/z 340 (M$^+$).

(b) Preparation of 17β-19,21-dinorchola-1,3,5(10)-trieno-[3,2,e]-1',2',3'-oxathiazine-2',2'-dioxide (36):

Using the procedure of Example 8, part (f), there was obtained from 3-hydroxy-17β-19,21-dinorchola-1,3,5(10)-triene-2-carboxaldehyde (29, 0.170 g, 0.5 mmol) after chromatography (n-hexane:EtOAc, 15:1→10:1, v/v) 0.125 g of 36 (62% yield), m.p. 155°–156° C.

$^1$H NMR: δ 8.57 (s, 1H, —CH=N—), 7.53 (s, 1H, aromatic), 6.98 (s, 1H, aromatic), 0.90 (t, 3H, 24-CH$_3$), 0.62 (s, 3H, 18-CH$_3$); MS (EI): m/z 401 (M$^+$). HRMS calcd. for C$_{23}$H$_{32}$N$_1$O$_3$S$_1$, 402.2103; found, 402.2100.

EXAMPLE 15

Preparation of 19-Norpregna-1,3,5(10),17(20),20-pentaeno-[3,2,e]-1',2',3'-oxathiazine-2',2'-dioxide (40)

Scheme 9

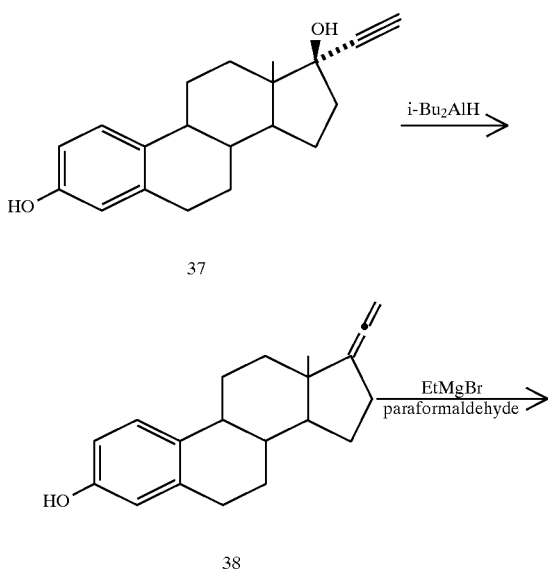

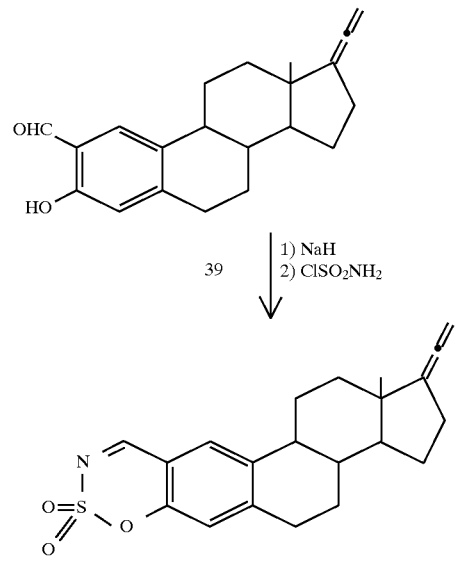

(a) Synthesis of 3-hydroxy-19-norpregna-1,3,5(10),17 (20),20-pentaene (38):

To a solution of ethynylestradiol (37, 10.37 g, 35 mmol) in THF (500 mL) was added diisobutylaluminum hydride (245 ml, 1.0M solution in toluene), and stirred for 24 h at reflux. The reaction mixture was quenched with MeOH at 0° C. and added saturated aqueous NaCl (ca 200 mL). The supernatant was decanted, and dried (Na$_2$SO$_4$). The desiccant was filtered and the solvent was evaporated at reduced pressure. The residue was purified by column chromatography (silica gel) using CHCl$_3$:THF (20:1→10:1, v/v) to afford 7.56 g of 38 (77% yield), m.p. 113°–115° C.

$^1$H NMR: δ 7.17 (d, 1H, aromatic), 6.72–6.53 (m, 2H, aromatic), 5.05–4.85 (s, 1H, —OH), 4.80–4.63 (m, 2H, =C=CH$_2$), 0.91 (s, 3H, 18-CH$_3$).

(b) Synthesis of 3-hydroxy-19-norpregna-1,3,5(10),17 (20),20-pentaene-2-carboxaldehyde (39):

To a suspension of magnesium (0.250 g, 10.0 mmol) in THF (2.5 mL) was added bromoethane (1.1 mL, 14 mmol) dissolved in THF (2.5 mL) at room temperature. 3-Hydroxy-19-norpregna-1,3,5(10),17(20),20-pentaene (38, 0.560 g, 2.0 mmol) dissolved in THF (5.0 mL) was added to the reaction mixture, and stirring continued for 30 min. The solvent was removed at reduced pressure, and to the residue were added benzene (25 mL), hexamethylphosphoric triamide (0.95 mL, 5.0 mmol) and paraformaldehyde (0.830 g). Stirring was continued for 3 h at 80° C. After the reaction mixture was cooled to room temperature, 5N HCl (10 mL) was added and the mixture extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:AcOEt (20:1→10:1, v/v) to afford 0.530 g of 39 (86% yield), m.p. 97°–99° C.

$^1$H NMR: δ 10.78 (s, 1H, —OH), 9.82 (s, 1H, —CHO), 7.43 (s, 1H, aromatic), 6.70 (s, 1H, aromatic), 4.83–4.65 (m, 2H, =C=CH$_2$), 0.91 (s, 3H, 18-CH$_3$); MS (EI): m/z 308 (M$^+$).

(c) Synthesis of 19-norpregna-1,3,5(10), 17(20),20-pentaeno-[3,2,e]-1',2',3'-oxathiazine-2',2'-dioxide (40):

To a solution of chlorosulfonyl isocyanate (0.23 mL, 2.5 mmol) in CH$_2$Cl$_2$ (1.0 mL) was added formic acid (0.5 mL of a CH$_2$Cl$_2$ solution, 5.0M, 2.5 mmol) at 0° C. The reaction mixture was warmed to room temperature and stirred for 1 h. To a solution of 3-hydroxy-19-norpregna-1,3,5(10),17 (20),20-pentaene-2-carboxaldehyde (39, 0.154 g, 0.5 mmol) in DMF (3.0 mL) was added sodium hydride (0.100 g of a mineral oil dispersion, 60%, 3.0 mmol) at 0° C. The reaction mixture was stirred for 1 h, the pre-prepared reagent was added, and stirring continued for 2 h at 0° C. and additional 1 h at room temperature. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (15:1→10:1, v/v) to afford 0.148 g of 40 (80% yield), m.p. 133°–135° C.

$^1$H NMR: δ 8.58 (s, 1H, —CH=N—), 7.54 (s, 1H, aromatic), 6.99 (s, 1H, aromatic), 4.88–4.65 (m, 1H, =C=CH$_2$), 0.91 (s, 3H, 18-CH$_3$); MS (EI): m/z 369 (M$^+$). HRMS calcd. for C$_{21}$H$_{24}$N$_1$O$_3$S$_1$, 370.1477; found, 370.1494.

EXAMPLE 16

Scheme 10

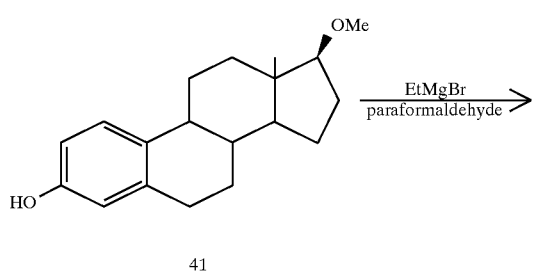

41

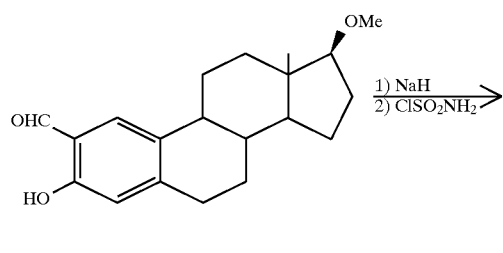

42

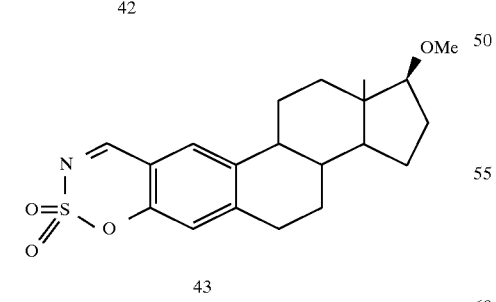

43

(a) Preparation of 3-hydroxy-17β-methoxyestra-1,3,5(10)-triene-2-carboxaldehyde (42):

To a suspension of magnesium (0.110 g 4.5 mmol) in THF (1.0 mL) was added bromoethane (0.50 mL, 6.6 mmol) dissolved in THF (1.0 mL) at room temperature. 3-Hydroxy-17β-methoxyestra-1,3,5(10)-triene (41, 0.258 g, 0.90 mmol;

synthesized by the method of Coombs et al., *Steroids* 6(6):841–844 (1965)), dissolved in THF (3.0 mL) was added to the reaction mixture, and stirring continued for 30 min. The solvent was removed at reduced pressure, and to the residue were added benzene (10 mL, hexamethylphosphoric triamide (0.40 mL, 2.1 mmol) and paraformaldehyde (0.370 g). Stirring was continued for 2 h at 80° C. After the reaction mixture was cooled to room temperature, 5N HCl (5.0 mL) was added and the mixture extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:AcOEt (10:1→8:1, v/v) to afford 0.221 g of 42 (78% yield), m.p. 120°–121° C.

$^1$H NMR: δ 10.77 (s, 1H, —OH), 9.81 (s, 1H, —CHO), 7.42 (s, 1H, aromatic), 6.70 (s, 1H, aromatic), 3.38 (s, 3H, 17β-OCH$_3$), 3.32 (t, 1H, 17α-H), 0.80 (s, 3H, 18-CH$_3$). MS (EI): m/z 314 (M+).

(b) Preparation of 17β-methoxyestra-1,3,5(10)-trieno-[3,2,e]-1',2',3'-oxathiazine-2',2'-dioxide (43):

To a solution of chlorosulfonyl isocyanate (0.23 mL, 2.5 mmol) in CH$_2$Cl$_2$ (1.0 mL) was added formic acid (0.5 mL of a CH$_2$Cl$_2$ solution, 5.0M, 2.5 mmol) at 0° C. The reaction mixture was warmed to room temperature and stirred for 1 h. To a solution of 3-hydroxy-17β-methoxyestra-1,3,5(10)-triene-2-carboxaldehyde (42, 0.157 g, 0.5 mmol) in DMF (3.0 mL) was added sodium hydride (0.100 g of a mineral oil dispersion, 60%, 3.0 mmol) at 0° C. The reaction mixture was stirred for 1 h, the preprepared reagent was added, and stirring continued for 3 h at 0° C. The reaction mixture was quenched with saturated aqueous NH$_4$Cl at 0° C. and extracted with EtOAc. The combined organic layers were washed with H$_2$O, then with saturated aqueous NaCl, and dried (Na$_2$SO$_4$). The desiccant was filtered and the solvent was evaporated at reduced pressure. The residue was purified by column chromatography (silica gel) using n-hexane:EtOAc (3:1→2:1, v/v) to afford 0.087 g of the starting material 42 (55% yield) and 0.074 g of 43 (39% yield), m.p. 172°–173° C.

$^1$H NMR: δ 8.57 (s, 1H, —CH=N—), 6.99 (s, 1H, aromatic), 6.99 (s, 1H, aromatic), 3.38 (s, 3H, 17β-OCH$_3$), 3.33 (t, 1H, 17α-H), 0.80 (s, 3H, 18-CH$_3$); MS (EI): m/z 375 (M$^+$). HRMS calcd. for C$_{20}$H$_{26}$N$_1$O$_4$S$_1$, 376.1583; found, 376.1603.

EXAMPLE 17

Preparation of [17(20)E]-Propylideneestra-1,3,5(10)-trieno-[3,2,e]-1',2',3'-oxathiazine-2,2'-dioxide (49)

Scheme 11

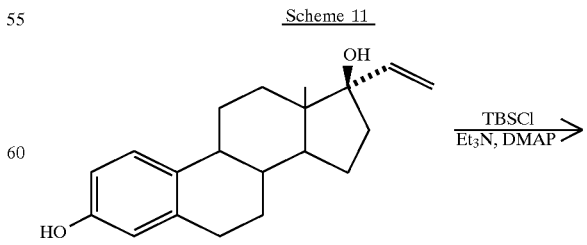

44

-continued
Scheme 11

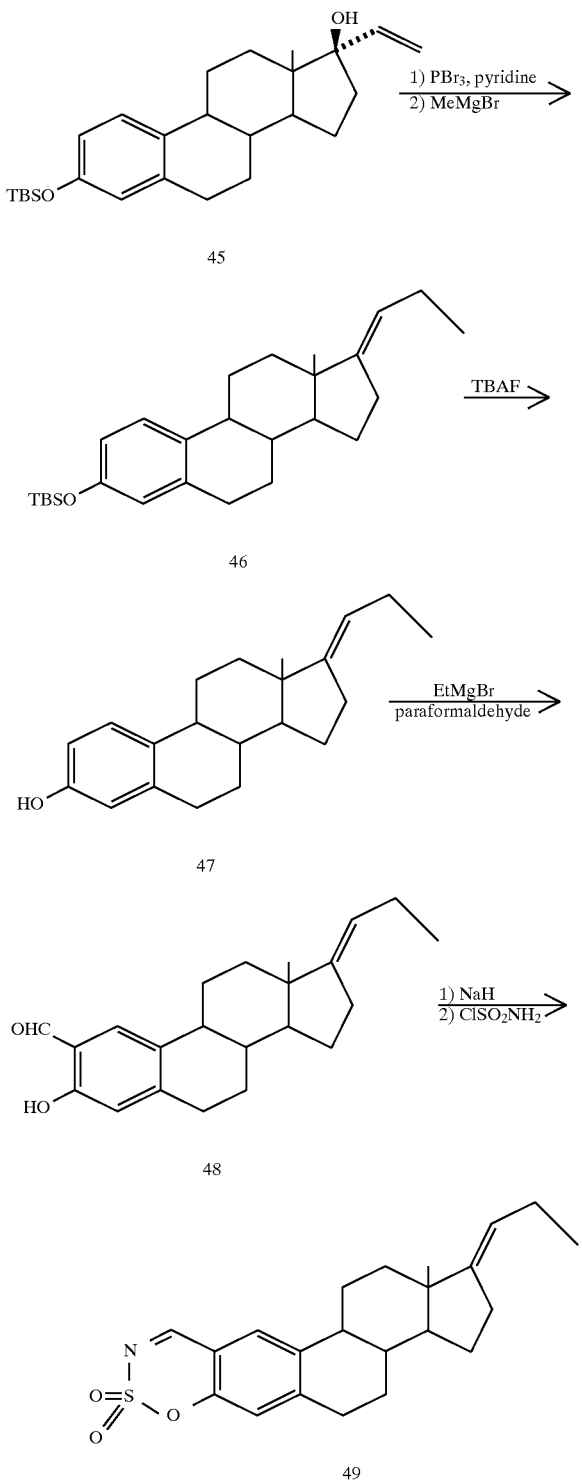

(a) Synthesis of 3-tert-butyldimethylsilyloxy-17 α-ethenylestra-1,3,5(10)-trien-17β-ol (45):

To a solution of 17β-ethenylestradiol (44, 0.298 g, 1.0 mmol) in $CH_2C_2$ (5.0 mL) and THF (1.0 mL) were added triethylamine (0.35 mL, 2.5 mmol), tert-butyldimethylchlorosilane (0.226 g, 1.5 mmol) and 4-dimethylaminopyridine (0.0006 g, 0.05 mmol) at room temperature. The reaction mixture was stirred for 2 days, diluted with EtOAc, washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (5:1→3:1, v/v) to afford 0.358 g of 45 (87% yield), m.p. 127°–128° C.

$^1$H NMR: δ 7.10 (d, 1H, aromatic), 6.67–6.52 (m, 2H, aromatic), 6.12 (dd, 1H, C$\underline{H}$=CH$_2$), 5.25–5.13 (m, 2H, —CH=C$\underline{H}_2$), 0.97 (S, 9H, —C(CH$_3$)$_3$), 0.95 (s, 3H, 18-CH$_3$), 0.18 (s, 6H, —Si(CH$_3$)$_2$).

(b) Synthesis of 3-tert-butyldimethylsilyloxy-[17(20)E]-propylideneestra-1,3,5(10)-triene (46):

To a solution of phosphorous tribromide (4.5 mL of a $CH_2Cl_2$ solution, 1.0M, 4.5 mmol) in toluene (6.0 mL) was added a solution of 3-tert-butyldimethylsilyloxy-17α-ethenylestra-1,3,5(10)-trien-17β-ol (45, 1.86 g, 4.5 mmol) and pyridine (0.40 mL, 5.0 mmol) in toluene (25 mL) at 0° C. The reaction mixture was stirred for 2 h, quenched with $H_2O$ and extracted with EtOAc. The combined organic layers were washed with $H_2O$, saturated aqueous NaCl, and then dried ($Na_2SO_4$). The desiccant was filtered and the solvent was evaporated at reduced pressure. The residue was dissolved in THF (20 mL) and added methylmagnesium-bromide (7.5 mL of a $Et_2O$ solution, 3.0M, 22.5 mmol) at 0° C. The reaction mixture was stirred for 19 h at room temperature, and quenched with $H_2O$ at 0° C. and extracted with EtOAc. The combined organic layers were washed with $H_2O$, saturated aqueous NaCl, and then dried ($Na_2SO_4$). The residue was purified by column chromatography (silica gel) using n-hexane:CHCl$_3$ (5:1→3:1, v/v) to afford 1.06 g of 46 (57% yield), m.p. 59°–60° C.

$^1$H NMR: δ 7.13 (d, 1H, aromatic), 6.66–6.51 (m, 2H, aromatic), 5.08–4.95 (m, 1H, =C$\underline{H}$CH$_2$), 0.98 (s, 9H, —C(CH$_3$)$_3$), 0.93 (t, 3H, 23-CH$_3$), 0.78 (s, 3H, 18-CH$_3$), 0.18 (s, 6H, —Si(CH$_3$)$_2$).

(c) Synthesis of [17(20)E]-propylideneestra-1,3,5(10)-trien-3-ol (47):

To a solution of 3-tert-butyldimethylsilyloxy-[17(20)E]-propylideneestra-1,3,5(10)-triene (46, 0.821 g, 2.0 mmol) in THF (20 mL) was added tetrabutylammonium fluoride (2.4 mL of a THF solution, 1.0M, 2.4 mmol) at 0° C. The reaction mixture was stirred for 1 h, diluted with EtOAc, washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (10:1→5:1, v/v) to afford 0.598 g of 47 (100% yield), m.p. 105°–106° C.

$^1$H NMR: δ 7.17 (d, 1H, aromatic), 6.67–6.52 (m, 2H, aromatic), 5.06–4.95 (m, 1H, =C$\underline{H}$CH$_2$), 4.53 (s, 1H, —OH), 0.95 (t, 3H, 23-CH$_3$), 0.78 (s, 3H, 18-CH$_3$); MS (EI): m/z 296 (M$^+$).

(d) Synthesis of 3-hydroxy-[17(20)E]-propylideneestra-1,3,5(10)-triene-2-carboxaldehyde (48):

To a suspension of magnesium (0.123 g, 5.0 mmol) in THF (1.5 mL) was added bromoethane (0.53 mL, 7.0 mmol) dissolved in THF (1.5 mL) at room temperature. [17(20)E]-Propylideneestra-1,3,5(10)-trien-3-ol (47, 0.297 g, 1.0 mmol) dissolved in THF (3.0 mL) was added to the reaction mixture, and stirring was continued for 30 min. The solvent was removed at reduced pressure. To the residue were added benzene (10 mL), hexamethylphosphoric triamide (0.46 mL, 2.5 mmol) and paraformaldehyde (0.410 g). Stirring was continued for 1 h at 80° C. After the reaction mixture was cooled to room temperature, 1N HCl (5.0 mL) was added and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (30:1→15:1, v/v) to afford 0.319 g of 48 (98% yield).

$^1$H NMR: δ 10.77 (s, 1H, —OH), 9.82 (s, 1H, —CHO), 7.44 (s, 1H, aromatic), 6.70 (s, 1H, aromatic), 5.06–4.98 (m, 1H, =C<u>H</u>CH$_2$), 0.96 (t, 3H, 23-CH$_3$), 0.79 (s, 3H, 18-CH$_3$); MS (EI): m/z 324 (M$^+$).

(e) Synthesis of [17(20)E]-propylideneestra-1,3,5(10)-trieno-[3,2,e]-1',2',3'-oxathiazine-2,2'-dioxide (49):

To a solution of chlorosulfonyl isocyanate (0.32 mL, 3.5 mmol) in $CH_2Cl_2$ (1.2 mL) was added formic acid (0.7 mL of a $CH_2Cl_2$ solution, 5.0M, 3.5 mmol) at 0° C. The reaction mixture was warmed to room temperature and stirred for 1 h. To a solution 3-hydroxy-[17(20)E]-propylideneestra-1,3,5(10)-triene-2-carboxaldehyde (48, 0.227 g, 0.70 mmol) in DMF (4.0 mL) was added sodium hydride (0.140 g of a mineral oil dispersion, 60%, 3.5 mmol) at 0° C. The reaction mixture was stirred for 1 h, the chlorosulfonyl isocyanate in formic acid was added, and stirring continued for 4 h at 0° C. The reaction mixture was quenched with saturated aqueous $NH_4Cl$ at 0° C. and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (10:1→5:1, v/v) to afford 0.056 g of the starting material 48 (25% yield) and 0.145 g of 49 (54% yield), m.p. 170°–171° C.

$^1$H NMR: δ 8.58 (s, 1H, —CH=N—), 7.55 (s, 1H, aromatic), 6.99 (s, 1H, aromatic), 5.10–4.97 (m, 1H, =C<u>H</u>CH$_2$), 0.96 (t, 3H, 23-CH$_3$), 0.79 (s, 3H, 18-CH$_3$); MS (EI): m/z 385 (M$^+$).

EXAMPLE 18

Preparation of [17(20)E]-Carbethoxy-methylideneestra-1,3,5(10)-trieno-[3,2,e]-1',2',3'-oxathiazine-2',2'-dioxide (54)

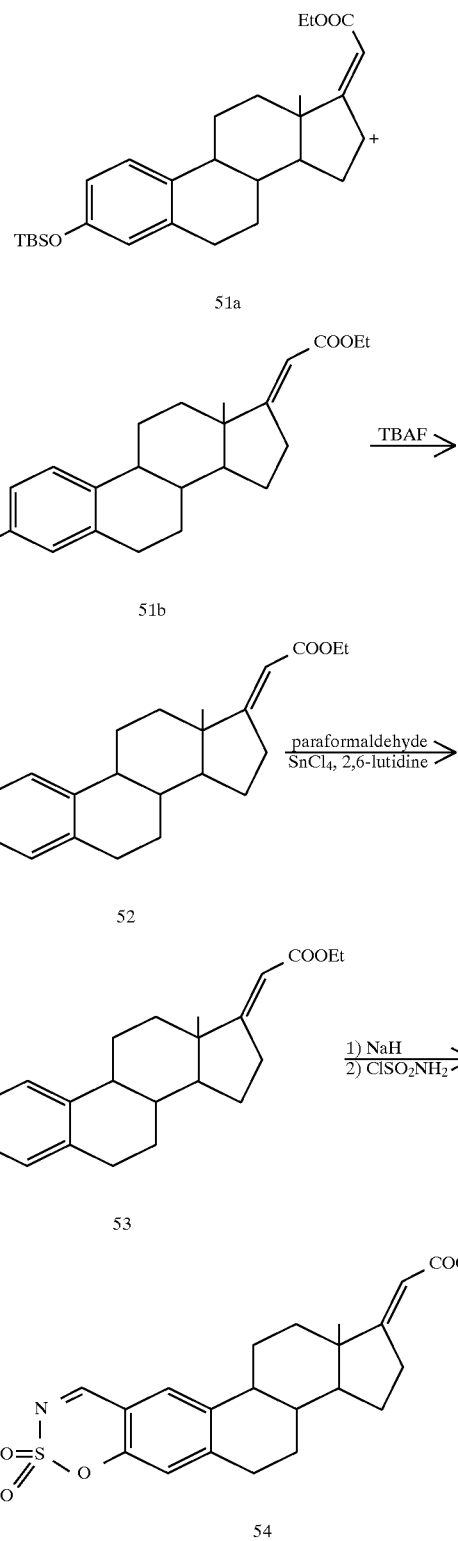

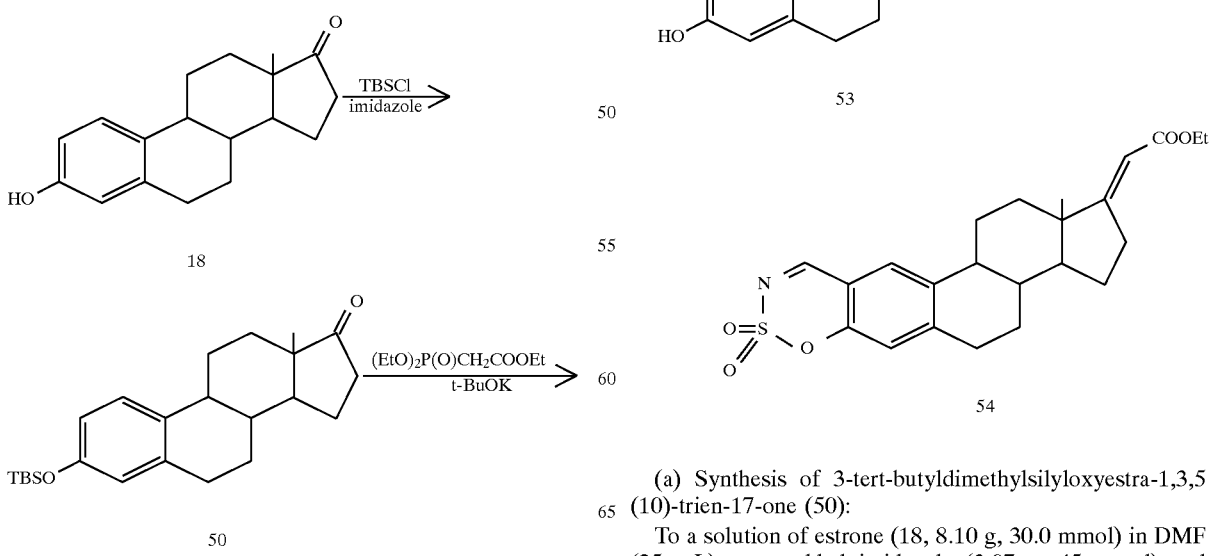

(a) Synthesis of 3-tert-butyldimethylsilyloxyestra-1,3,5(10)-trien-17-one (50):

To a solution of estrone (18, 8.10 g, 30.0 mmol) in DMF (25 mL) were added imidazole (3.07 g, 45 mmol) and tert-butyldimethylchlorosilane (5.42 g, 36 mmol) at room temperature. The reaction mixture was stirred for 18 h and then quenched with H$_2$O (100 mL). The precipitate was collected by filtration and washed with H$_2$O to afford 11.4 g of 50 (99% yield), m.p. 171°–172° C.

$^1$H NMR: δ 7.12 (d, 1H, aromatic), 6.67–6.55 (m, 2H, aromatic), 0.98 (s, 9H, —C(CH$_3$)$_3$), 0.91 (s, 3H, 18-CH$_3$), 0.19 (s, 6H, —Si(CH$_3$)$_2$).

(b) Synthesis of ethyl 3-tert-butyldimethylsilyloxy-[17(20)Z]-19-norpregna-1,3,5(10),17(20)-tetraen-21-oate (51a) and ethyl 3-tert-butyldimethylsilyloxy-[17(20)E]-19-norpregna-1,3,5(10),17(20)-tetraen-21-oate (51b):

To a solution of triethylphosphonoacetate (3.17 mL, 16 mmol) in THF (40 mL) was added potassium tert-butoxide (1.68 g, 15 mmol) at room temperature. The reaction mixture was stirred for 30 min, and 3-tert-butyldimethylsilyloxyestra-1,3,5(10)-trien-17-one (50, 1.92 g, 5.0 mmol) was added. The stirring continued for 2 days at reflux. The reaction mixture was cooled to room temperature and quenched with saturated aqueous NH$_4$Cl followed by extraction with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (40:1→30:1, v/v) to afford 0.473 g of 51a (21% yield) and 1.26 g of 51b (55% yield), m.p. 109°–110° C.

51a: $^1$H NMR: δ 7.12 (d, 1H, aromatic), 6.65–6.50 (m, 2H, aromatic), 5.70–5.63 (m, 1H, =CH—COOEt), 4.23–4.05 (m, 2H, —COOCH$_2$), 1.29 (t, 3H, —COOCH$_2$CH$_3$), 1.04 (S, 3H, 18-CH$_3$), 0.98 (s, 9H, —C(CH$_3$)$_3$), 0.18 (s, 6H, —Si(CH$_3$)$_2$).

51b: $^1$H NMR: δ 7.12 (d, 1H, aromatic), 6.65–6.50 (m, 2H, aromatic), 5.59 (s, 1H, =CH—COOEt), 4.16 (q, 2H, —COOCH$_2$CH$_3$), 1.29 (t, 3H, —COOCH$_2$CH$_3$), 0.98 (s, 9H, —C(CH$_3$)$_3$), 0.86(s, 3H, 18-CH$_3$), 0.19 (s, 6H, —Si(CH$_3$)$_2$).

(c) Synthesis of ethyl 3-hydroxy-[17(20)E]-19-norpregna-1,3,5(10),17(20)-tetraen-21-oate (52):

To a solution of ethyl 3-tert-butyldimethylsilyoxy-[17(20)E]-19-norpregna-1,3,5(10),17(20)-tetraen-21-oate (51b, 1.00 g, 2.2 mmol) in THF (15 mL) was added tetrabutylammonium fluoride (2.5 mL of a THF solution, 1.0M, 2.5 mmol) at 0° C. The reaction mixture was stirred for 1 h, diluted with EtOAc, washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (5:1→3:1, v/v) to afford 0.727 g of 52 (97% yield), m.p. 153°–154° C.

$^1$H NMR: δ 7.15 (d, 1H, aromatic), 6.68–6.53 (m, 2H, aromatic), 5.59 (s, 1H, =CH—COOEt), 4.77–4.65 (m, 1H,—OH), 4.17 (q, 2H, —COOCH$_2$CH$_3$), 1.29 (t, 3H, —COOCH$_2$CH$_3$), 0.86 (s, 3H, 18-CH$_3$); MS (EI): m/z 340 (M$^+$).

(d) Synthesis of ethyl 2-formyl-3-hydroxy-[17(20)E]-19-norpregna-1,3,5(10),17(20)-tetraen-21-oate (53):

To a solution of ethyl 3-hydroxy-[17(20)E]-19-norpregna-1,3,5(10),17(20)-tetraen-21-oate (53, 0.681 g, 2.0 mmol) in 1,2-dichloroethane (15 mL) and toluene (7.0 mL) were added 2,6-lutidine (0.12 ml, 10 mmol) and tin (IV) chloride (0.4 mL of a n-heptane solution, 1.0M, 0.4 mmol), and the mixture was stirred for 30 min at room temperature. To the reaction mixture was added paraformaldehyde (200 mg) and stirring was continued for 18 h at 100° C. After the reaction mixture was cooled to room temperature, 1N HCl (20 mL) was added and the mixture extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (7:1→5:1, v/v) to afford 0.224 g of 53 (30% yield), m.p. 135°–136° C.

$^1$H NMR: δ 10.78 (s, 1H, —OH), 9.82 (s, 1H, —CHO), 7.43 (s, 1H, aromatic), 6.71 (s, 1H, aromatic), 5.60 (s, 1H, =CH—COOEt), 4.17 (q, 2H, —COOCH$_2$CH$_3$), 1.30 (t, 3H, —COOCH$_2$CH$_3$), 0.88 (s, 3H, 18-CH$_3$); MS (EI): m/z 368 (M$^+$).

(e) Synthesis of [17(20)E]-carbethoxymethylideneestra-1,3,5(10)-trieno-[3,2,e]-1',2',3'-oxathiazine-2',2'-dioxide (54):

To a solution of chlorosulfonyl isocyanate (0.14 mL, 1.5 mmol) in CH$_2$Cl$_2$ (0.6 mL) was added formic acid (0.3 mL of a CH$_2$Cl$_2$ solution, 5.0M, 1.5 mmol) at 0° C. The reaction mixture was warmed to room temperature and stirred for 1 h. To a solution ethyl 2-formyl-3-hydroxy-[17(20)E]-19-norpregna-1,3,5(10),17(20)-tetraen-21-oate (53, 0.110 g, 0.30 mmol) in DMF (3.0 mL) was added sodium hydride (0.060 g of a mineral oil dispersion, 60%, 1.5 mmol) at 0° C. The reaction mixture was stirred for 1 h, the chlorosulfonyl isocyanate in formic acid was added, and stirring continued for 2 h at 0° C. The reaction mixture was quenched with saturated aqueous NH$_4$Cl at 0° C. and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (5:1→3:1, v/v) to afford 0.057 g of the starting material 53 (52% yield) and 0.043 g of 54 (33% yield), m.p. 223°–224° C.

$^1$H NMR: δ 8.58 (s, 1H, —CH=N—), 7.54 (s, 1H, aromatic), 7.00 (s, 1H, aromatic), 5.61 (s, 1H, =CH—COOEt), 4.17 (q, 2H—COOCH$_2$CH$_3$), 1.30 (t, 3H, —COOCH$_2$CH$_3$), 0.88 (s, 3H, 18-CH$_3$); MS (EI): m/z 429 (M$^+$).

EXAMPLE 19

Preparation of 17-Dicyanomethylideneestra-1,3,5 (10)-trieno-[3,2,e]-1',2',3'-oxathiazine-2',2'-dioxide (66)

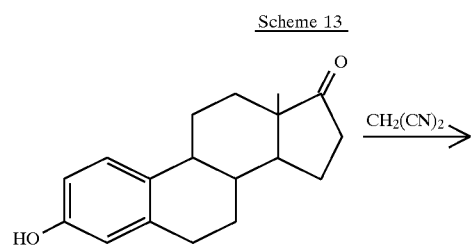

18

-continued
Scheme 13

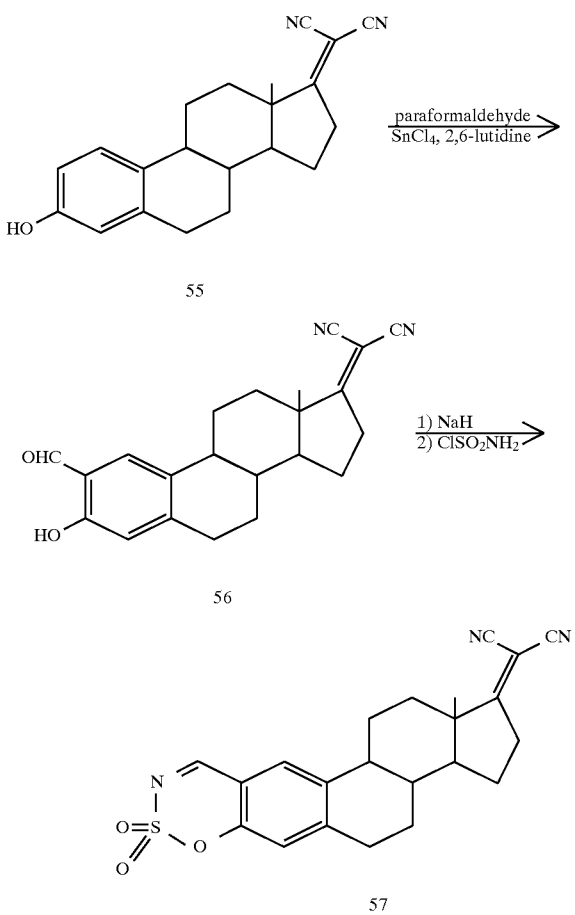

(a) Synthesis of 20-cyano-3-hydroxy-19-norpregna-1,3,5 (10),17(20)-tetraene-21-nitrile (55):

To a suspension of estrone (18, 1.35 g, 5.0 mmol) in benzene (35 mL) and acetic acid (5.0 mL) were added malononitrile (1.65 g, 40 mmol) and β-alanine (0.535 g, 6.0 mmol), and stirring was continued for 19 h at reflux. After the reaction mixture was cooled to room temperature, $H_2O$ was added and the reaction mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was washed with $Et_2O$ to afford 1.46 g of 55 (92% yield), m.p. >250° C.

$^1$H NMR: δ 7.13 (d, 1H, aromatic), 6.70–6.53 (m, 2H, aromatic), 1.07 (s, 3H, 18-$CH_3$); MS (EI): m/z 318 ($M^+$).

(b) Synthesis of 20-cyano-2-formyl-3-hydroxy-19-norpregna-1,3,5(10),17(20)-tetraene-21-nitrile (56):

To a solution of 20-cyano-3-hydroxy-19-norpregna-1,3,5 (10),17(20)-tetraene-21-nitrile (55, 0.637 g, 2.0 mmol) in $CH_2Cl_2$ (15 mL) and toluene (7.0 mL) were added 2,6-lutidine (0.12 ml, 1.0 mmol) and tin (IV) chloride (0.4 mL of a n-heptane solution, 1.0M, 0.4 mmol), and stirring was continued for 30 min at room temperature. To the reaction mixture was added paraformaldehyde (200 mg) and stirring continued for 18 h at 100° C. After the reaction mixture was cooled to room temperature, 1N HCl (20 mL) was added and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:THF (5:1→3:1, v/v) to afford 0.313 g of 56 (45% yield), m.p. >250° C.

$^1$H NMR: δ 10.81 (s, 1H, —OH), 9.84 (s, 1H, —CHO), 7.41 (d, 1H, aromatic), 6.72 (s, 1H, aromatic), 1.09 (s, 3H, 18-$CH_3$); MS (EI): m/z 346 ($M^+$).

(c) Synthesis of 17-dicyanomethylideneestra-1,3,5(10)-trieno-[3,2,e]-1',2',3'-oxathiazine-2',2'-dioxide (57):

To a solution of chlorosulfonyl isocyanate (0.14 mL, 1.5 mmol) in $CH_2Cl_2$ (0.6 mL) was added formic acid (0.3 mL of a $CH_2Cl_2$ solution, 5.0M, 1.5 mmol) at 0° C. The reaction mixture was warmed to room temperature and stirred for 1 h. To a solution of 20-cyano-2-formyl-3-hydroxy-19-norpregna-1,3,5(10),17(20)-tetraene-21-nitrile (56, 0.104 g, 0.30 mmol) in DMF (3.0 mL) was added sodium hydride (0.060 g of a mineral oil dispersion, 60%, 1.5 mmol) at 0° C. The reaction mixture was stirred for 1 h, the chlorosulfonyl isocyanate in formic acid was added, and stirring continued for 3 h at 0° C. The reaction mixture was quenched with saturated aqueous $NH_4Cl$ at 0° C. and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:THF (5:1→2:1, v/v) to afford 0.040 g of the starting material 65 (39% yield) and 0.027 g of 66 (22% yield), m.p. >250° C.

$^1$H NMR: δ 8.61 (s, 1H, —CH=N—), 7.53 (s, 1H, aromatic), 7.02 (s, 1H, aromatic), 1.10 (s, 3H, 18-$CH_3$); MS (EI): m/z 407 ($M^+$).

EXAMPLE 20

Biological Evaluation: Procedures and Results

A. Procedures:

Test for the Effects of Inhibitors on Estrone Sulfatase Activity in MCF-7 Cells:

Reagents: MCF-7 human breast cancer cells were supplied by the American Type Culture Collection, Rockville, Md. Eagle's minimum essential medium (MEM) and fetal calf serum (FCS) were purchased from Sigma Chemical Company, St. Louis, Mo. [4-$^{14}$C] Estrone, [6,7-$^3$H] estradiol and [6,7-$^3$H(N)] estrone sulfate were obtained from New England Nuclear Research Products, Boston, Mass.

Estrone Sulfatase Assay with Intact Cells. The procedure of Duncan et al., Cancer Res. 53:298–303 (1993) was followed. MCF-7 cells were seeded in 60×15 mm culture dishes at 1×10$^5$ cells/dish and maintained in 4.0 mL of MEM containing 2 mM of glutamine and 5% of FCS. The cells were incubated at 37° C. in a 5% $CO_2$/95% air atmosphere and 100% humidity, with the medium changed every third day. When the cells reach 80% confluency, the intact monolayers were washed once with Earl's balanced salt solution and incubated in 4.0 mL of serum-free MEM containing the substrate ($^3$H-estrone sulfate, 7 pmol, 9×10$^5$ dpm) and inhibitor dissolved in ethanol or ethanol alone. The final ethanol concentration was always be below 1%. The incubation continued for 24 h. 2.0 mL of medium was transferred into separate tubes containing 7×10$^3$ dpm of $^{14}$C-estrone. The mixture was vortexed vigorously for 60 s with 5 mL of toluene. After phase separation, 2.0 mL of the organic phase was transferred into a counting vial for scintillation counting. The amount of estrone sulfate hydrolyzed was calculated on the basis of the $^3$H counts obtained, with the added $^{14}$C-estrone used to correct for recovery through the extraction procedure.

The cells remaining in each culture dish were washed with saline once and then scraped with 1.0 mL of 0.5N NaOH into 10×75 mm tubes. The cell pellets in each tube were incubated at 50° C. for 20 min. to ensure that digestion was complete and that all proteins became soluble. An aliquot was then taken for protein determination by Lowry's method (Lowry et al., J. Biol. Chem. 193:265–275 (1951)).

The amount of estrone sulfate hydrolyzed with the inhibitor relative to that without the inhibitor was evaluated to give the percentage of inhibition.

In Vivo Efficacy Studies Using MCF-7 Cells in Nude Mice:

For in vivo evaluation, human xenografts were used in nude (athymic) mice, in the context of a solid tumor assay.

MCF-7 human breast carcinomas in nude mice were used as the model for evaluating the estrone sulfatase inhibitors. The protocol followed was essentially that of Yue et al., J. Steroid Biochem. 44:671–673 (1993). Because MCF-7 cells are known to require supplementation with estradiol to sustain progressive growth in athymic nude mice (Soule et al., Cancer Lett. 10:177–189 (1980)), estrone sulfate was used for supplemental estrogen in the model studies. The enzyme inhibitors were administered by intravenous injection, oral gavage, and intraperitoneal administration, and comparative efficacy of the various compounds were evaluated using these different routes.

Materials:

Female BALB/c athymic mice 4–6 weeks of age were supplied by Charles River Breeding Laboratories, Boston, Mass. MCF-7 cells for the in vitro cell growth inhibition assay were obtained from the American Type Culture Collection, Rockville, Md., and cultured under the same conditions as described above for the sulfatase assay.

Tumor Growth Inhibition Assay (see Santer et al. (1990), supra, Yue et al., supra, and Noel et al., Biochem. Pharmacol. 43:1263–1267 (1992):

The athymic mice were housed five per cage in controlled conditions of light and humidity and received food and water ad libitum throughout the entire experiment. The mice were quarantined for three working days before use in experiments. Prior to the initiation of the antitumor experiments, the mice were housed for seven days to familiarize them with the experimental environment. Temperature was maintained at 72±5° F., with relative humidity at 35–70% and a 12-h light/dark cycle. The mice were fed certified Purina rodent chow and drinking water ad libitum. The source water was recirculated, deionized, UV-treated, and filtered (5-µm filter).

At the beginning of the experiment, all but five of the mice underwent oophorectomies to eliminate the endogenous level of estrogen. After all animals recovered from surgery, all mice in the study received 5 µmol of estrone sulfate daily via gavage or subcutaneous (sc) injection. The dosing of estrone sulfate was carried out throughout the entire experiment. Seven days after the animals began treatment with estrone sulfate, each mouse was be injected sc twice (once in each flank) with 2.5×10$^6$ MCF-7 cells suspended in 0.1 mL of serum-free tissue culture medium to induce tumor growth. The growth rate was determined by measuring the tumors with calipers weekly. Tumor volumes were calculated according to the formula $4/3\pi r_1^2, r_2$, where $r_1$ and $r_2$ represent the tumor radii. When the average tumor volume per mouse reached approximately 200 mm$^3$, animals began to receive various doses of estrone sulfatase inhibitors dissolved in 0.1 mL of phosphate buffered saline (PBS). Dosing was by oral gavage, intravenous injection, and intraperitoneal injection; daily dosing with estrone sulfatase inhibitors was continued throughout the remainder of the experiment. The estrone sulfatase inhibitors not soluble in aqueous solutions were dissolved in EtOH first and diluted with PBS to obtain the appropriate concentrations of inhibitor but keeping the concentration of EtOH below 1%.

For each test compound, the mice were divided into several groups with five animals in each group. These groups were as follows: intact control group receiving PBS alone; oophorectomized control group receiving PBS alone; and oophorectomized treatment groups receiving various doses of estrone sulfatase inhibitors.

The mice were treated with the estrone sulfatase inhibitors for 60 days, and the tumor growth rate was monitored weekly. The change in tumor volume in the treatment groups relative to that in the oophorectomized control group gave the percent inhibition of a given inhibitor.

TABLE 1

EFFICACY OF ESTRONE SULFATASE INHIBITORS ON MCF-7 HUMAN BREAST CARCINOMA XENOGRAFTS IN ATHYMIC MICE[a]

| Week | Tumor Volume[b] | |
|---|---|---|
| | Compound 6 | Control |
| 0 | 133.6 ± 15.9 | 96.5 ± 5.2 |
| 1 | 185.8 ± 16.5 | 184.1 ± 26.3 |
| 2 | 191.3 ± 25.1 | 191.2 ± 36.1 |
| 3 | 181.8 ± 27.8 | 232.9 ± 46.4 |
| 4 | 234.0 ± 50.7 | 299.5 ± 54.3 |
| 5 | 285.8 ± 47.7 | 349.0 ± 46.2 |

[a]Mice were dosed by i.p. injection at 1.0 mg/mouse/day for 5 weeks.
[b]Mean ± S.E., mm$^3$

TABLE 2

Estrone Sulfatase Inhibition Assay Results

| Compound | Sulfatase Assay Concentration | Sulfatase Assay % Inhibition |
|---|---|---|
| ESTRONE SULFATASE INHIBITION ASSAY RESULTS | | |
| 4 | 12 nM | 50 |
| 6 | 9.3 nM | 50 |
| 10 | 20 nM | 50 |
| 11 | 820 nM | 50 |
| 13 | 44 nM | 50 |
| 14 | 15 µM | 50 |
| 17 | 50 nM | 50 |
| 30 | 72 nM | 50 |
| 31 | 63 nM | 50 |
| 32 | 58 nM | 50 |
| 33 | 720 nM | 50 |
| 34 | 45 nM | 50 |
| 35 | 120 nM | 50 |
| 36 | 590 nM | 50 |
| 40 | 74 nM | 50 |
| 43 | 50 nM | 50 |

We claim:

1. A compound having the structural formula (I)

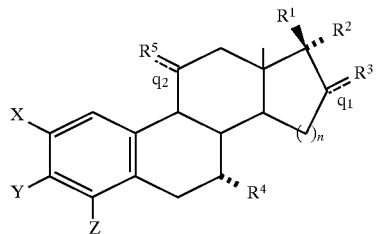

(I)

wherein:

n is 1;

$R^1$ and $R^2$ are different, and are selected from the group consisting of hydrogen, lower alkyl, lower alkynyl, and $OR^6$ where $R^6$ is hydrogen, lower alkyl or —(CO)—$R^7$ where $R^7$ is lower alkyl, or wherein $R^1$ and $R^2$ together form =O, =S, or =C($R^8R^9$) in which $R^8$ and $R^9$ are independently selected from the group consisting of hydrogen, —CHO, lower alkyl, and cyano, or together form a =$CH_2$ substituent;

$R^3$ is hydrogen, halogen or lower alkyl, or, when the dotted line at $q_1$ indicates the presence of a double bond, is $CH_2$;

$R^4$ is selected from the group consisting of hydrogen and lower alkyl;

$R^5$ is selected from the group consisting of hydrogen, hydroxyl, lower alkyl, lower alkenyl, lower alkoxy, and aryl, or when the dotted line at $q_2$ indicates the presence of a double bond, is $CH_2$; and Y and Z are linked to form an oxathiazine dioxide ring or a dihydro-oxathiazine dioxide ring, if dihydro-oxathiazine, having a substituent $R^{10}$ on the carbon atom adjacent to the A ring, wherein $R^{10}$ is hydrogen, lower alkyl, lower alkynyl or monocyclic aryl, and X is hydrogen, cyano, lower alkyl, lower alkenyl, lower alkynyl, lower alkoxy, nitro, —$COOR^{11}$, or —($CH_2$)$NR^{12}R^{13}$ wherein $R^{11}$, $R^{12}$ and $R^{13}$ are independently hydrogen or lower alkyl, and pharmaceutically acceptable salts and esters thereof.

2. The compound of claim 1, wherein one of $R^1$ and $R^2$ is hydrogen, and the other is selected from the group consisting of hydroxyl, lower alkyl, lower alkoxy, lower acyl and ethynyl.

3. The compound of claim 1, wherein $R^1$ and $R^2$ together form =O or =C($R^8R^9$) in which $R^8$ and $R^9$ are independently selected from the group consisting of hydrogen, —CHO, methyl, ethyl, n-propyl, and cyano, or together form a =$CH_2$ substituent.

4. The compound of any one of claims 1, 2 or 3, wherein Y and Z are linked to form an oxathiazine dioxide ring.

5. The compound of any one of claims 1, 2 or 3, wherein Y and Z are linked to form a dihydro-oxathiazine dioxide ring, and $R^{10}$ is hydrogen, methyl, ethynyl or phenyl.

6. A method for inhibiting the enzymatic activity of estrone sulfatase comprising contacting the enzyme with an effective estrone sulfatase inhibiting amount of a compound having the structural formula (I)

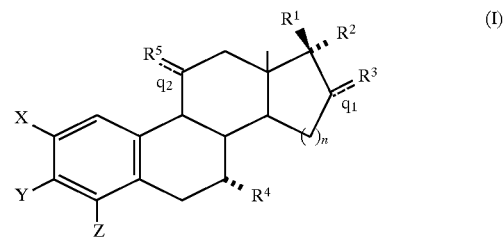

(I)

wherein:

n is 1;

$R^1$ and $R^2$ are different, and are selected from the group consisting of hydrogen, lower alkyl, lower alkynyl, and $OR^6$ where $R^6$ is hydrogen, lower alkyl or —(CO)—$R^7$ where $R^7$ is lower alkyl, or wherein $R^1$ and $R^2$ together form =O, =S, or =C($R^8R^9$) in which $R^8$ and $R^9$ are independently selected from the group consisting of hydrogen, —CHO, lower alkyl, and cyano, or together form a =$CH_2$ substituent;

$R^3$ is hydrogen, halogen or lower alky, or, when the dotted line at $q_1$ indicates the presence of a double bond, is $CH_2$;

$R^4$ is selected from the group consisting of hydrogen and lower alkyl;

$R^5$ is selected from the group consisting of hydrogen, hydroxyl, lower alkyl, lower alkenyl, lower alkoxy, and aryl, or when the dotted line at $q_2$ indicates the presence of a double bond, is $CH_2$; and Y and Z are linked to form an oxathiazine dioxide ring or a dihydro-oxathiazine dioxide ring, if dihydro-oxathiazine, having a substituent $R^{10}$ on the carbon atom adjacent to the A ring, wherein $R^{10}$ is hydrogen, lower alkyl, lower alkynyl or monocyclic aryl, and X is hydrogen, cyano, lower, alkyl, lower alkenyl, lower alkynyl, lower alkoxy, nitro, —$COOR^{11}$, or —($CH_2$)$NR^{12}R^{13}$ wherein $R^{11}$, $R^{12}$ and $R^{13}$ are independently hydrogen or lower alkyl, or with a pharmaceutically acceptable salt or ester thereof.

7. The method of claim 6, wherein, in the compound of formula (I), one of $R^1$ and $R^2$ is hydrogen, and the other is selected from the group consisting of hydroxyl, lower alkyl, lower alkoxy, lower acyl and ethynyl.

8. The method of claim 6, wherein, in the compound of formula (I), $R^1$ and $R^2$ together form =O or =C($R^8R^9$) in which $R^8$ and $R^9$ are independently selected from the group consisting of hydrogen, —CHO, methyl, ethyl, n-propyl, or together form a =$CH_2$ substituent.

9. The method of any one of claims 6, 7 or 8, wherein, in the compound of formula (I), Y and Z are linked to form an oxathiazine dioxide ring.

10. The method of any one of claims 6, 7 or 8, wherein, in the compound of formula (I), Y and Z are linked to form a dihydro-oxathiazine dioxide ring and $R^{10}$ is hydrogen, methyl, ethynyl or phenyl.

11. A method for treating an individual with an estrogen-dependent disorder, comprising administering to the individual a pharmacologically effective amount of a compound of structural formula (I)

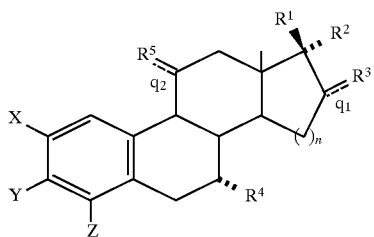

wherein:

n is 1,

R$^1$ and R$^2$ are different, and are selected from the group consisting of hydrogen, lower alkyl, lower alkynyl, and OR$^6$ where R$^6$ is hydrogen, lower alkyl or —(CO)—R$^7$ where R$^7$ is lower alkyl, or wherein R$^1$ and R$^2$ together form =O, =S, or =C(R$^8$R$^9$) in which R$^8$ and R$^9$ are independently selected from the group consisting of hydrogen, —CHO, lower alkyl, and cyano, or together form a =CH$_2$ substituent;

R$^3$ is hydrogen, halogen or lower alkyl, or, when the dotted line at q$_1$ indicates the presence of a double bond, is CH$_2$;

R$^4$ is selected from the group consisting of hydrogen and lower alkyl;

R$^5$ is selected from the group consisting of hydrogen, hydroxyl, lower alkyl, lower alkenyl, lower alkoxy, and aryl, or when the dotted line at q$_2$ indicates the presence of a double bond, is CH$_2$; and either X and Y are linked to form an oxathiazine dioxide ring or a dihydro-oxathiazine dioxide ring, if dihydro-oxathiazine, having a substituent R$^{10}$ on the carbon atom adjacent to the A ring, wherein R$^{10}$ is hydrogen, lower alkyl, lower alkynyl or monocyclic aryl, and Z is hydrogen, or Y and Z are linked to form an oxathiazine dioxide ring or a dihydro-oxathiazine dioxide ring, if dihydro-oxathiazine, having a substituent R$^{10}$ on the carbon atom adjacent to the A ring, wherein R$^{10}$ is hydrogen, lower alkyl, lower alkynyl or monocyclic aryl, and X is hydrogen, cyano, lower alkyl, lower alkenyl, lower alkynyl, lower alkoxy, nitro, —COOR$^{11}$, or —(CH$_2$)NR$^{12}$R$^{13}$ wherein R$^{11}$, R$^{12}$ and R$^{13}$ are independently hydrogen or lower alkyl, or a pharmaceutically acceptable salt or ester thereof.

12. The method of claim 11, wherein, in the compound of formula (I), one of R$^1$ and R$^2$ is hydrogen, and the other is selected from the group consisting of hydroxyl, lower alkyl, lower alkoxy, lower acyl and ethynyl.

13. The method of claim 11, wherein, in the compound of formula (I), R$^1$ and R$^2$ together form =O or =C(R$^8$R$^9$) in which R$^8$ and R$^9$ are independently selected from the group consisting of hydrogen, —CHO, methyl, ethyl, n-propyl, and cyano, or together form a =CH$_2$ substituent.

14. The method of any one of claims 11, 12 or 13, wherein, in the compound of formula (I), X and Y are linked to form an oxathiazine dioxide ring.

15. The method of any one of claims 11, 12 or 13, wherein, in the compound of formula (I), X and Y are linked to form a dihydro-oxathiazine dioxide ring and R$^{10}$ is hydrogen, methyl, ethynyl or phenyl.

16. The method of any one of claims 11, 12 or 13, wherein, in the compound of formula (I), Y and Z are linked to form an oxathiazine dioxide ring.

17. The method of any one of claims 11, 12 or 13, wherein, in the compound of formula (I), Y and Z are linked to form a dihydro-oxathiazine dioxide ring and R$^{10}$ is hydrogen, methyl, ethynyl or phenyl.

18. A pharmaceutical composition comprising an effective estrone sulfatase inhibiting amount of the compound of claim 1 in combination with a pharmaceutically acceptable carrier.

19. A pharmaceutical composition comprising an effective estrone sulfatase inhibiting amount of the compound of claim 2 in combination with a pharmaceutically acceptable carrier.

20. A pharmaceutical composition comprising an effective estrone sulfatase inhibiting amount of the compound of claim 3 in combination with a pharmaceutically acceptable carrier.

21. A pharmaceutical composition comprising an effective estrone sulfatase inhibiting amount of the compound of claim 4 in combination with a pharmaceutically acceptable carrier.

22. A pharmaceutical composition comprising an effective estrone sulfatase inhibiting amount of the compound of claim 5 in combination with a pharmaceutically acceptable carrier.

* * * * *